United States Patent
Bard (12)

(10) Patent No.: US 6,225,075 B1
(45) Date of Patent: May 1, 2001

(54) DNA ENCODING STEROL METHYLTRANSFERASE

(75) Inventor: Martin Bard, Carmel, IN (US)

(73) Assignee: Advanced Research and Technology Institute, Inc., Indianapolis, IN (US)

( * ) Notice: Subject to any disclaimer, the term of this patent is extended or adjusted under 35 U.S.C. 154(b) by 0 days.

(21) Appl. No.: 09/041,718

(22) Filed: Mar. 13, 1998

(51) Int. Cl.[7] .............................. C12Q 1/48; C12N 1/14; C07H 21/04

(52) U.S. Cl. .................. 435/15; 435/254.1; 435/254.11; 435/254.22; 536/23.2

(58) Field of Search ......................... 435/254.1, 254.11, 435/254.22, 15; 536/23.2

(56) References Cited

PUBLICATIONS

Ator, M.A., et al., "Mechanism and Inhibition of Delta[24]–Sterol Methyltransferase from *Candida albicans* and *Candida tropicalis*", *Biochemistry*, 28, 9633–9640 (Dec. 12, 1989).

Ator, M.A., et al., "Synthesis, Specificity, and Antifungal Acitivity of Inhibitors of the *Candida albicans* Delta[24]–Sterol Methyltransferase", *Journal of Medical Chemistry*, 35, 100–106 (Jan. 10, 1992).

Barrett–Bee, K., et al., "Ergosterol Biosynthesis Inhibition: A Target for Antifungal Agents", *Acta Biochimica Polonica*, 42, 465–480 (1995).

Bouvier–Nave, P., et al., "Identification of cDNAs Encoding Sterol Methyl–Transferases Involved in the Second Methylation Step of Plant Sterol Biosynthesis", *European Journal of Biochemistry*, 246, 518–529 (1997).

Gaber, R.F., et al., "The Yeast Gene ERG6 is Required for Normal Membrane Function but is not Essential for Biosynthesis of the Cell–Cycle–Sparking Sterol", *Molecular and Cellular Biology*, 9, 3447–3456 (Aug. 1989).

Hardwick, K.G., et al., "SED6 is Identical to ERG6, and Encodes a Putative Methyltransferase Required for Ergosterol Synthesis", *Yeast*, 10, 265–269 (1994).

Kennedy, M.A., et al., "Cloning of the *Candida albicans* ERG6 Gene", Programs and Abstracts of the 112th Annual Meeting of the Indiana Academy of Science, Depauw University, Indianapolis, IN, p. 86 (Nov. 7–8, 1996).

Kleinhans, F.W., et al., "ESR Determinations of Membrane Permeability in a Yeast Sterol Mutant", *Chemistry and Physics of Lipids*, 23, 143–154 (1979).

Lees, N.D., et al., "Biochemistry and Molecular Biology of Sterol Synthesis in *Saccharomyces cerevisiae*", In: *Biochemistry and Function of Sterols*, Parish, E.J., (ed.), CRC Press, Inc., Boca Raton, FL, p. 85–99 (1997).

Mercer, E.I., "Inhibitors of Sterol Biosynthesis and Their Applications", *Prog. Lipid Res.*, 32, 357–416 (1993).

Nes, W.D., et al., "Substrate–Based Inhibitors of the (S)–Adenosyl–L–Methionine: Delta[24(25)]–to Delta[24(28)]–Sterol Methyl Transferase from *Saccharomyces cerevisiae*", *Archives of Biochemistry and Biophysics*, 342, 68–81 (Jun. 1, 1997).

Sanglard, D., et al., "Susceptibilities of *Candida albicans* Multidrug Transporter Mutants of Various Antifungal Agents and Other Metabolic Inhibitors", *Antimicrobial Agents and Chemotherapy*, 40, 2300–2305 (Oct. 1996).

Vogel, J.P., et al., "Brefeldin A Causes a Defect in Secretion in *Saccharomyces cerevisiae*", *Journal of Biological Chemistry*, 268, 3040–3043 (Feb. 15, 1993).

Welihinda, A.A., et al., "Mutations in LIS1 (ERG6) Gene Confer Increased Sodium and Lithium Uptake in *Saccharomyces cerevisiae*", *Biochimica et Biophysica Acta*, 1193, 107–117 (1994).

White, T. C., "Antifungal Drug Resistance in *Candida albicans*", *ASM News*, 63, 427–433 (Aug. 1997).

Rudinger (Jun. 1976) Characteristics of the amino acids as components of a peptide hormone sequence. In: Peptide Hormones. Ed. J. A. Parsons. University Park Press, Baltimore, MD. pp. 1–7.*

Ngo et al. (Jan. 1994) Computational complexity, protein structure prediction, and the Ilevinthal paradox. In: The Protein Folding Problem and Tertiary Structure Prediction. Eds. Merz et al. Birkhauser et al. Boston, MA. pp. 491–495.*

Thornton et al. (Aug. 1995) Protein Engineering: Editorial Overview. Current Opinion in Biotechnology 6(4): 367–369.*

Wallace (Apr. 1993) Understanding cytochrome c function: engineering protein structure by semisynthesis. The FASEB Journal 7: 505–515.*

Hussain et al. (Jan. 1991) Characterization of PDR4, a *Saccharomyces cerevisiae* gene that confers pleiotropic drug resistance in high–copy number. Gene 101: 149–152.*

Husselstein et al. (Feb. 1996) Transformation of *Saccharomyces cerevisiae* with a cDNA encoding a sterol C–methyltransferase from *Arabidopsis thaliana* results in the synthesis of 24–ethyl sterols. FEBS Letters 381: 87–92.*

* cited by examiner

*Primary Examiner*—Einar Stole
(74) *Attorney, Agent, or Firm*—Schwegman, Lundberg, Woessner & Kluth, P.A.

(57) ABSTRACT

The invention provides an isolated and purified nucleic acid molecule encoding a *Candida albicans* sterol methyltransferase (ERG6). Also provided is a *C. albicans* strain or isolate that has reduced levels of sterol methyltransferase as a result of the disruption of at least one sterol methyltransferase gene. Preferred isolates are more susceptible to a number of sterol synthesis and metabolic inhibitors relative to wild type isolates. Further provided are methods to identify sterol methyltransferase inhibitors and methods to screen for antifungals or metabolic inhibitors which are not normally permeable to the fungal cell.

17 Claims, 9 Drawing Sheets

| Amino Acid | Codon |
|---|---|
| Phe | UUU, UUC |
| Ser | UCU, UCC, UCA, UCG, AGU, AGC, CUG |
| Tyr | UAU, UAC |
| Cys | UGU, UGC |
| Leu | UUA, UUG, CUU, CUC, CUA |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

FIG. 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

```
C. a. ERG 6    1    MSPVQLAEK-NYERDEQETKALHGESY-KKTGLSAL    34
S. c. ERG 6    1    MSETELR-----KRQAQFTRELHGDDIGKKTGLSAL    31
A. t. ERG 6    1    MDSLTLFFTGALVAVGIY-WFLCVLGPAERKGKRAV    35
T. a. ERG 6    1    MFVFCLCTRCRICRVSSFPVLELFMFIHLSYFFLVL    36

C. a. ERG 6   35    IAKSKDAASVAAEGYFKHWDGGISKDDEEKRLNDYS    70
S. c. ERG 6   32    MSKNNSAQKEAVQKYLRNWDGRTDKDAEERRLEDYN    67
A. t. ERG 6   36    DLSGGSISAEKVQDNYKQYWSFFRRPKEIETAEKVP    71
T. a. ERG 6   37    LLILGQFFFTRYEKYHGYYGGK-----EESRKSNYT    67

C. a. ERG 6   71    QLTHHYYNLVTDFYEYGWGSSFHFSRYYKGEAFRQA   106
S. c. ERG 6   68    EATHSYYNVVTDFYEYGWGSSFHFSRFYKGESFAAS   103
A. t. ERG 6   72    DFVDTFYNLVTDIYEWGWGQSFHFSPSIPGKSHKDA   107
T. a. ERG 6   68    DMVNKYYDLATSFYEYGWGESFHFAHRWNGESLRES   103

C. a. ERG 6  107    TARHEHFLAHKMNLNENMKVLDVGCGVGGPGREITR   142
S. c. ERG 6  104    IARHEHYLAYKAGIQRGDLVLDVGCGVGGPAREIAR   139
A. t. ERG 6  108    TRLHEEMAVDLIQVKPGQKILDVGCGVGGPMRAIAS   143
T. a. ERG 6  104    IKRHEHFLALQLELKPGMKVLDVGCGIGGPLREIAR   139

C. a. ERG 6  143    FTDCEIVGLNNDYQIERANHYAKKYHLDHKLSYVK   178
S. c. ERG 6  140    FTGCNVIGLNNDYQIAKAKYYAKKYNLSDQMDFVK   175
A. t. ERG 6  144    HSRANVVGITINEYQVNRARLHNKKAGLDALCEVVC   179
T. a. ERG 6  140    FSSTSVTGLNNDYQITRGKALNRSVGLGATCDFVK   175

C. a. ERG 6  179    GDFMQMDFEPESFDAVYATEATVHAPVLEGVYSEIY   214
S. c. ERG 6  176    GDFMKMDFEENTFDKVYAIEATCHAPKLEGVYSEIY   211
A. t. ERG 6  180    GNFLQMPFDDNSFDGAYSIEATCHAPKLEEVYAEIY   215
T. a. ERG 6  176    ADFMKMPFSDNTFDAVYATEATCHAPDPVGCYKEIY   211

C. a. ERG 6  215    KVLKPGGIFGVYEWVMTDKYDETNEEHRKIAYGIEV   250
S. c. ERG 6  212    KVLKPGGTFAVYEWVMTDKYDENNPEHRKIAYEIEL   247
A. t. ERG 6  216    RVLKPGSMYVSYEWVTTEKFKAEDDEHVEVIQGIER   251
T. a. ERG 6  212    RVLKPGQCFAVYEWCITDHYDPNNATHKRIKDEIEL   247

C. a. ERG 6  251    GDGIPKMYSRKVAEQALKNVGFEIEYQKDLADVDDE   286
S. c. ERG 6  248    GDGIPKMFHVDVARKALKNCGFEVLVSEDLADNDDE   283
A. t. ERG 6  252    GDALPGLRAYVDIAETAKKVGFEIVKEKDLASPPAE   287
T. a. ERG 6  248    GNGLPDIRSTRQCLQAVKDAGFEVIWDKDLAE-DSP   282

C. a. ERG 6  287    IPWYYPLSGDLKFCQTFGDYLTVFRTSRIGRFITTE   322
S. c. ERG 6  284    IPWYYPLTGEWKYVQNLANLATFERTSYLGRQFTTA   319
A. t. ERG 6  288    -PWW--------------TRLKMGRLAYWRNHI    305
T. a. ERG 6  283    LPWYLPL-DPSRFS-----LSSFRLTTVGRIITRN   311

C. a. ERG 6  323    SVGLMEKIGLAPKGSKQVTHALEDAAVNLVEGGRQK   358
S. c. ERG 6  320    MVTVMEKLGLAPEGSKEVTAALENAAVGLVAGGKSK   355
A. t. ERG 6  306    VVQILSAVGVAPKGTVDVHEMLFKTADCLTRGGETG   341
T. a. ERG 6  312    MVKVLEYVGLAPEGSQRVSSFLEKAAEGLVEGGKKE   347

C. a. ERG 6  359    LFTPMMLYVVRKPLEK                      374
S. c. ERG 6  356    LFTPMMLFVARKPENAETPSQTSQEATQ          383
A. t. ERG 6  342    IFSPMHMILCRKPESPEESS                  361
T. a. ERG 6  348    IFTPVYFFVRKPLSE                       363
```

FIG. 6

DNA ENCODING STEROL METHYLTRANSFERASE

STATEMENT OF GOVERNMENT RIGHTS

This invention was made with a grant from the Government of the United States of America (Grant No. DAMD17-95-1-5067). The Government may have certain rights in the invention.

BACKGROUND OF THE INVENTION

The frequency of occurrence of human fungal infections has been increasing over the past decade in response to a combination of factors (Georgopapadakou et al., 1994). These factors include advances in invasive surgical techniques which allow for opportunistic pathogen access, the administration of immunosuppressive agents employed in transplantation, and an increase in the number of immunosuppressed patients resulting from chemotherapy and disease states such as AIDS. The threat to human health is further compounded by the increased frequency with which resistance to the commonly employed antifungal agents is occurring.

Currently, the most common antifungals include the polyenes and the azoles. The polyenes bind to ergosterol, the fungal membrane sterol, and induce lethal cell leakage (Brajtburg et al., 1990). However, polyenes often have negative side effects and resistance to polyenes has been reported (Hebeka et al., 1965; Powderley et al., 1988). The azoles are fungistatic agents that inhibit the cytochrome P450-mediated removal of the C-14 methyl group from the ergosterol precursor, lanosterol (Vanden Bossche et al., 1987). Resistance to azoles has been reported in *Candida albicans* (Clark et al., 1996; Sanglard et al., 1996; Sanglard et al., 1995; White, 1997a; White, 1997b) as well as in other species of Candida (Moran et al., 1997; Parkinson et al., 1995), and in other fungal pathogens, including species of Histoplasma (Wheat et al., 1997), Cryptococcus (Lamb et al., 1997; Venkateswarlu al., 1997), and Aspergillus (Denning et al., 1997).

The pathway for fungal sterol biosynthesis is one target for antifungal development. In particular, fungal genes that catalyze a step in sterol biosynthesis that is not found in cholesterol biosynthesis (Pinto et al., 1983) are of interest in this regard. One such fungal gene is the sterol methyltransferase gene (ERG6). Non-recombinant *Saccharomyces cerevisiae* erg6 mutants have been available for some time (Molzhan et al., 1972). The *S. cerevisiae* ERG6 gene has been isolated, and recombinant strains prepared (i.e., via genetic engineering) in which the gene has been disrupted (Gaber et al., 1989). Although the absence of the ERG6 gene product in *S. cerevisiae* was not lethal, it did result in several severely compromised phenotypes (Bard et al., 1978; Kleinhans et al., 1979; Lees et al., 1979; Lees et al., 1980).

*S. cerevisiae* erg6 mutants have been shown to have diminished growth rates as well as limitations on utilizable energy sources (Lees et al., 1980), reduced mating frequency (Gaber et al., 1989), altered membrane structural features (Kleinhans et al., 1979; Lees et al., 1979), and low transformation rates (Gaber et al., 1989). In addition, several lines of evidence have indicated that *S. cerevisiae* erg6 mutants have severely altered permeability characteristics. This has been demonstrated using dyes (Bard et al., 1978), cations (Bard et al., 1978), and spin labels used in electron paramagnetic resonance studies (Kleinhans et al., 1979). These early observations have been corroborated recently by the cloning of the *S. cerevisiae* LIS1 gene (Welihinda et al., 1994), mutants of which were selected on the basis of hypersensitivity to sodium and lithium. Sequencing of LIS1 has indicated identity to ERG6. In addition, studies using the Golgi inhibitor, brefeldin A, have routinely employed erg6 mutants because of their remarkably increased permeability to the compound (Vogel et al., 1993). However, as *S. cerevisiae* and *Candida albicans* differ in their ability to survive and grow on various sterol intermediates, and as *S. cerevisiae* is rarely the cause of a human disease, it was unknown whether the ERG6 gene in the common fungal pathogen, *C. albicans*, effected similar properties.

Thus, a continuing need exists for fungal genes and strains that can aid in the identification of agents that increase the susceptibility of pathogenic fungi to conventional antifungal or anti-metabolic agents.

SUMMARY OF THE INVENTION

The present invention provides an isolated nucleic acid segment comprising a nucleic acid sequence encoding a *Candida albicans* sterol methyltransferase (ERG6), a biologically active variant or subunit thereof. As described hereinbelow, the *Candida albicans* ERG6 gene was isolated by complementation of a *Saccharomyces cerevisiae* erg6 mutant using a *Candida albicans* genomic library. Preferably, the sterol methyltransferase of the invention comprises SEQ ID NO:2, which is encoded by a DNA having SEQ ID NO:1. Thus, the invention further provides isolated, purified recombinant *Candida albicans* sterol methyltransferase, a biologically active variant or subunit thereof, e.g., a polypeptide having SEQ ID NO:2. Methods to isolate and purify sterol methyltransferase are known to the art (see, for example, Ator et al., 1989).

ERG6 can be used in a method to identify antifungals targeted specifically to sterol methyltransferase. Therefore, the invention also provides a method to identify inhibitors of fungal sterol methyltransferase. The method comprises contacting an amount of isolated, purified recombinant *Candida albicans* sterol methyltransferase, or a biologically active variant or subunit thereof, with an amount of an agent. The activity of the sterol methyltransferase in the presence of the agent is then determined or detected relative to an amount of sterol methyltransferase not contacted with the agent.

The isolation and characterization of a *Candida albicans* ERG6 gene also permits the preparation of recombinant *Candida albicans* isolates that lack a functional sterol methyltransferase, e.g., isolates which have decreased or reduced amounts of sterol methyltransferase, or lack sterol methyltransferase activity. Inhibiting the functional ERG6 gene product may make the cell hypersensitive to exogenous compounds, and thus could increase the effectiveness of new or existing antifungals. Thus, as described hereinbelow, the first copy of the Candida ERG6 gene was disrupted by transforming a wild type isolate with the ura blaster system. The second copy of the Candida ERG6 gene was disrupted by ura blaster transformation or mitotic recombination. The resulting erg6 strains were shown to be more susceptible to a number of sterol synthesis and metabolic inhibitors including terbinafine, tridemorph, fenpropiomorph, fluphenazine, cycloheximide, cerulenin and brefeldin A, relative to the corresponding isolate of *Candida albicans* which encodes a functional sterol methyltransferase. No increase in susceptibility to azoles was noted.

Therefore, recombinant *Candida albicans* isolates lacking, or having reduced, sterol methyltransferase activity are useful in a method to identify antifungal agents that would otherwise have low or no ability to permeate the fungal cell membrane and thus may be overlooked as therapeutic agents. Moreover, the administration of inhibitors of the ERG6 gene product to a host organism having a fungal infection may make the fungal cell increasingly susceptible to antifungals or other agents which normally would be excluded, e.g., due to their lack of ability to permeate the cell, and may permit clinical treatment at lower dosages. Hence, the invention provides a method to enhance the efficacy of an agent such as an antifungal agent, comprising: administering to a mammal having, or at risk of having, a fungal infection, an amount of agent that inhibits *Candida albicans* sterol methyltransferase and an amount of an anti-fungal agent effective to inhibit or treat the infection. Preferably, the sterol methyltransferase inhibitor is administered in an amount that reduces or decreases the effective amount of the anti-fungal agent administered relative to the effective amount of the anti-fungal agent administered in the absence of the inhibitor.

Also provided is a method to identify inhibitors of fungal sterol methyltransferase. The method comprises contacting an isolate of a fungus, e.g., *Candida albicans*, with an amount of an agent, wherein the genome of the isolate has two functional sterol methyltransferase genes which are expressed so as to yield wild type levels of sterol methyltransferase. Then it is determined whether the agent inhibits the growth of the isolate or reduces the amount or activity of the sterol methyltransferase of the isolate, relative to a corresponding isolate having and expressing more than two copies of a functional sterol methyltransferase.

BRIEF DESCRIPTION OF THE FIGURES

FIG. 1. Codons for specified amino acids.

FIG. 2. Exemplary and preferred substitutions for variant *C. albicans* sterol methyltransferase (ERG6) polypeptide.

FIG. 5. The DNA sequence (SEQ ID NO:1) and corresponding inferred amino acid sequence (SEQ ID NO:2) of a *Candida albicans* ERG6 gene. The underlined region indicates the S-adenosyl-methionine binding site.

FIG. 6. Alignment of the amino acid sequences of the sterol methyltransferases from *Candida albicans* (C. a.; SEQ ID NO:2), *Saccharomyces cerevisiae* (S. c.; SEQ ID NO:3), *Arabidopsis thaliana* (A. t.; SEQ ID NO:4), and *Triticum ativum* (T a.; SEQ ID NO:5).

DETAILED DESCRIPTION OF THE INVENTION

Definitions

Figure 3:
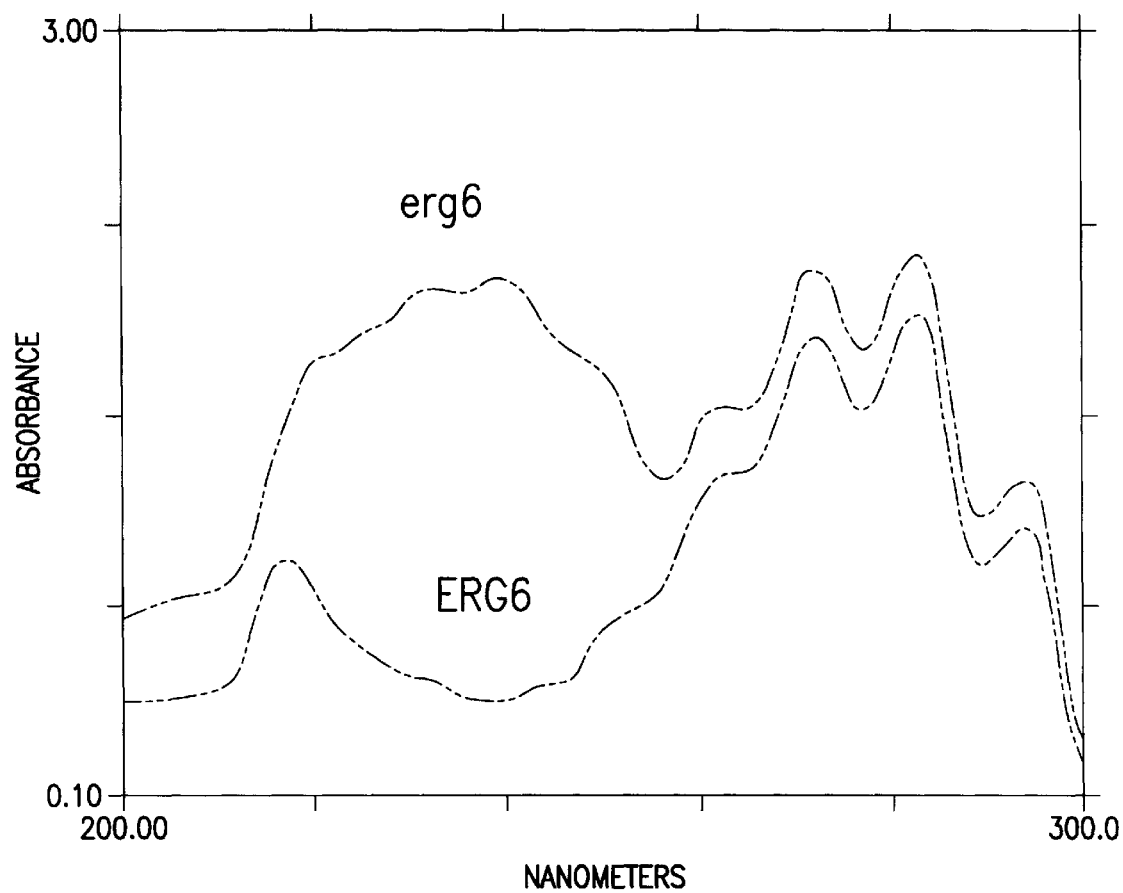
FIG. 3. UV scan of non-saponifiable sterols in which erg6 sterols containing a conjugated double bond in the sterol side chain show absorption maxima at 230 and 238 nm. Wild type strains containing the Candida ERG6 gene do not have the conjugated double bond system in the sterol side chain.

As used herein, a "variant" of a *C. albicans* sterol methyltransferase is a polypeptide that has at least about 70%, preferably at least about 80%, and more preferably at least about 90%, but less than 100%, contiguous amino acid sequence homology or identity to the amino acid sequence of the corresponding wild type *C. albicans* sterol methyltransferase polypeptide, e.g., SEQ ID NO:2. Thus, a variant sterol methyltransferase polypeptide of the invention may include amino acid residues not present in the corresponding wild type sterol methyltransferase polypeptide, and may include amino and/or carboxy-terminal or internal deletions or insertions relative to the corresponding wild type polypeptide. Variants of the invention include polypeptides having at least one D-amino acid. Preferably, the variant polypeptides of the invention are biologically active. A "biologically active" sterol methyltransferase of the invention has at least about 1%, more preferably at least about 10%, and more preferably at least about 50%, of the activity of the sterol methyltransferase having SEQ ID NO:2. Methods to determine the biological activity of sterol methyltransferase are well known to the art (see, for example, Ator et al., 1989).

Sterol methyltransferase polypeptides, variants or subunits thereof which are subjected to chemical modifications, such as esterification, amidation, reduction, protection and the like, are referred to as "derivatives."

As used herein, a "susceptible" isolate means that the isolate has decreased growth in the presence of a particular agent relative to the growth of the isolate in the absence of the agent.

A "recombinant" isolate of the invention is a strain or isolate of *C. albicans* that has been manipulated in vitro so as to alter, e.g., decrease or disrupt, the function or activity of the endogenous sterol methyltransferase. A "recombinant" isolate of the invention also includes a strain or isolate of *C. albicans* that has been manipulated in vitro so as to increase the amount or activity of sterol methyltransferase present in that isolate or strain.

As used herein, the terms "isolated and/or purified" refer to in vitro preparation, isolation and/or purification of a nucleic acid molecule or polypeptide of the invention, so that it is not associated with in vivo substances.

A "variant" nucleic acid molecule of the invention is a molecule that has at least about 70%, preferably about 80%, and more preferably about 90%, but less than 100%, contiguous nucleotide sequence homology or identity to the nucleotide sequence corresponding to a wild type *C. albi-*

*cans* sterol methyltransferase gene, e.g., SEQ ID NO:1. A variant sterol methyltransferase gene of the invention may include nucleotide bases not present in the corresponding wild type gene, e.g., 5', 3' or internal deletions or insertions such as the insertion of restriction endonuclease recognition sites, relative to the wild type gene.

A. Nucleic Acid Molecules of the Invention

1. Sources of the Nucleic Acid Molecules of the Invention

Sources of nucleotide sequences from which the present nucleic acid molecules encoding a *C. albicans* sterol methyltransferase, a subunit or a variant thereof, or the nucleic acid complement thereof, include total or polyA+ RNA from any isolate of *C. albicans* from which cDNAs can be derived by methods known in the art. Other sources of the nucleic acid molecules of the invention include genomic libraries derived from any *C. albicans* strain or isolate. Moreover, the present nucleic acid molecules may be prepared in vitro, or by subcloning at least a portion of a DNA segment that encodes a particular *C. albicans* sterol methyltransferase polypeptide.

2. Isolation of a Gene Encoding *C. albicans* Sterol Methyltransferase

A nucleic acid molecule encoding a *C. albicans* sterol methyltransferase polypeptide can be identified and isolated using standard methods, as described by Sambrook et al., *Molecular Cloning: A Laboratory Manual*, Cold Spring Harbor, N.Y. (1989). For example, reverse-transcriptase PCR (RT-PCR) can be employed to isolate and clone *C. albicans* sterol methyltransferase cDNAs. Oligo-dT can be employed as a primer in a reverse transcriptase reaction to prepare first-strand cDNAs from isolated RNA which contains RNA sequences of interest, e.g., total RNA isolated from human tissue. RNA can be isolated by methods known to the art, e.g., using TRIZOL™ reagent (GIBCO-BRL/Life Technologies, Gaithersburg, Md.). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7–8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., Cold Spring Harbor *Symp. Quant. Biol.*, 51, 263 (1987); Erlich, ed., *PCR Technology*, (Stockton Press, N.Y., 1989). Thus, PCR-based cloning approaches rely upon conserved sequences deduced from alignments of related gene or polypeptide sequences.

Primers are made to correspond to relatively highly conserved regions of polypeptides or nucleotide sequences which were identified and compared to generate the primers, e.g., by a sequence comparison of non-*C. albicans* sterol methyltransferase genes. One primer is prepared which is predicted to anneal to the antisense strand, and another primer prepared which is predicted to anneal to the sense strand, of a nucleic acid molecule which encodes a *C. albicans* sterol methyltransferase.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs.

Another approach to identify, isolate and clone DNAs which encode *C. albicans* sterol methyltransferase is to screen a cDNA or genomic *C. albicans* DNA library. Screening for DNA fragments that encode all or a portion of a DNA encoding *C. albicans* sterol methyltransferase can be accomplished by screening the library with a probe which has sequences that are highly conserved between genes believed to be related to *C. albicans* sterol methyltransferase, e.g., the homolog of *C. albicans* sterol methyltransferase from a different species, or by screening of plaques for binding to antibodies that recognize sterol methyltransferase. DNA fragments that bind to a probe having sequences which are related to *C. albicans* sterol methyltransferase, or which are immunoreactive with antibodies to *C. albicans* sterol methyltransferase, can be subcloned into a suitable vector and sequenced and/or used as probes to identify other DNAs encoding all or a portion of *C. albicans* sterol methyltransferase.

Yet another method to identify and isolate a DNA encoding a *C. albicans* sterol methyltransferase is to employ a complementation assay. Thus, erg6 mutants are transformed with either genomic DNA or cDNA of *C. albicans* and clones are identified that complement the erg6 mutation and/or are cycloheximide resistant, as described below.

As used herein, the terms "isolated and/or purified" refer to in vitro isolation of a nucleic acid molecule or polypeptide molecule from its natural cellular environment, and from association with other components of the cell, such as nucleic acid or polypeptide, so that it can be sequenced, replicated, and/or expressed. For example, "isolated *C. albicans* sterol methyltransferase nucleic acid" is RNA or DNA containing greater than 7, preferably 15, and more preferably 25 or more, sequential nucleotide bases that encode at least a portion of *C. albicans* sterol methyltransferase, or a variant thereof, or a RNA or DNA complementary thereto, or that is complementary or hybridizes, respectively, to RNA or DNA encoding *C. albicans* sterol methyltransferase or a variant thereof and remains stably bound under stringent conditions, as defined by methods well known in the art, e.g., in Sambrook et al., supra. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell.

As used herein "stringent conditions" means conditions that detect a nucleic acid molecule with at least 80%, preferably at least 90%, nucleotide sequence homology to the probe or primer sequence. See Sambrook et al., *Molecular Cloning: A Laboratory Manual*, Cold Spring Harbor Laboratory Press (2nd ed., 1989) for selection of hybridization and washing conditions for DNA:DNA, as well as DNA:RNA (Northern blot), stable and specific duplex formation. Stringent conditions include those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% sodium dodecylsulfate (SDS), and 10% dextran sulfate at 42° C., with washes at 42° C. in 0.2×SSC and 0.1% SDS.

An example of isolated *C. albicans* sterol methyltransferase nucleic acid is RNA or DNA that encodes *C. albicans* sterol methyltransferase and wherein the methyltransferase shares at least about 70%, preferably at least about 80%, and more preferably at least about 90%, sequence identity with at least a portion of the *C. albicans* sterol methyltransferase polypeptide having SEQ ID NO:2, e.g., a DNA molecule corresponding to SEQ ID NO:1.

As used herein, the term "recombinant nucleic acid" or "preselected nucleic acid," e.g., "recombinant DNA sequence or segment" or "preselected DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.*, 9, 6103 (1981), and Goeddel et al., *Nucleic Acids Res.*, 8, 4057 (1980). Therefore, "preselected DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular nucleic acid molecule.

3. Variants of the Nucleic Acid Molecules of the Invention

Nucleic acid molecules encoding amino acid sequence variants of *C. albicans* sterol methyltransferase are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of *C. albicans* sterol methyltransferase.

Oligonucleotide-mediated mutagenesis is a preferred method for preparing truncated forms and amino acid substitution variants of *C. albicans* sterol methyltransferase polypeptide, including variants that are truncated. This technique is well known in the art as described by Adelman et al., DNA, 2, 183 (1983). Briefly, *C. albicans* sterol methyltransferase DNA is altered by hybridizing an oligonucleotide encoding the desired mutation to a DNA template, where the template is the single-stranded form of a plasmid or bacteriophage containing the unaltered or native DNA sequence of *C. albicans* sterol methyltransferase. After hybridization, a DNA polymerase is used to synthesize an entire second complementary strand of the template that will thus incorporate the oligonucleotide primer, and will code for the selected alteration in the *C. albicans* sterol methyltransferase DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A.*, 75, 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.*, 153, 3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, N.Y. 1989). Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the *C. albicans* sterol methyltransferase, and the other strand (the original template) encodes the native, unaltered sequence of *C. albicans* sterol methyltransferase. This heteroduplex molecule is then transformed into a suitable host cell, usually a prokaryote such as *E. Coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for polypeptide production, generally an expression vector of the type typically employed for transformation of an appropriate host.

The method described immediately above may be modified so that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine triphosphate (dATP), deoxyriboguanosine triphosphate (dGTP), and deoxyribothymidine triphosphate (dTTP), is combined with a modified thiodeoxyribocytosine triphosphate called dCTP-(αS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS)

instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101.

For example, a preferred embodiment of the invention is an isolated and purified DNA molecule comprising a preselected DNA segment encoding *C. albicans* sterol methyltransferase having SEQ ID NO:2, wherein the DNA segment comprises SEQ ID NO:1, or variants of SEQ ID NO:1, having nucleotide substitutions which are "silent" (see FIG. 1). That is, when silent nucleotide substitutions are present in a codon, the same amino acid is encoded by the codon with the nucleotide substitution as is encoded by the codon without the substitution. For example, valine is encoded by the codon GTT, GTC, GTA and GTG. A variant of SEQ ID NO:2 at the fourth codon in the polypeptide (GTT in SEQ ID NO:1) includes the substitution of GTC, GTA or GTG for GTT. Other "silent" nucleotide substitutions in SEQ ID NO:1 which can encode *C. albicans* sterol methyltransferase having SEQ ID NO:2 can be ascertained by reference to FIG. 1 and page D1 in Appendix D in Sambrook et al., *Molecular Cloning: A Laboratory Manual* (1989), although unlike the vast majority of organisms, a CUG in *C. albicans* encodes serine, not leucine. Nucleotide substitutions can be introduced into DNA segments by methods well known to the art, see, for example, Sambrook et al., supra. Moreover, the nucleic acid molecules of the invention may be modified in a similar manner so as to result in *C. albicans* sterol methyltransferase polypeptides that have deletions, for example, the polypeptides are truncated at the C-terminus of *C. albicans* sterol methyltransferase. Such deletions can be accomplished by introducing a stop codon, i.e., UAA, UAG, or UGA, in place of a codon for an amino acid.

4. Chimeric Expression Cassettes and Host Cells Transformed Therewith

To prepare expression cassettes for transformation herein, the recombinant or preselected DNA sequence or segment may be circular or linear, double-stranded or single-stranded. A preselected DNA sequence which encodes an RNA sequence that is substantially complementary to a mRNA sequence encoding a sterol methyltransferase is typically a "sense" DNA sequence cloned into a cassette in the opposite orientation (i.e., 3' to 5' rather than 5' to 3'). Generally, the preselected DNA sequence or segment is in the form of chimeric DNA, such as plasmid DNA, that can also contain coding regions flanked by control sequences which promote the expression of the preselected DNA present in the resultant cell line.

As used herein, "chimeric" means that a vector comprises DNA from at least two different species, or comprises DNA from the same species, which is linked or associated in a manner which does not occur in the "native" or wild type of the species.

Aside from preselected DNA sequences that serve as transcription units for a sterol methyltransferase, or portions thereof, a portion of the preselected DNA may be untranscribed, serving a regulatory or a structural function. For example, the preselected DNA may itself comprise a promoter that is active in mammalian cells, or may utilize a promoter already present in the genome that is the transformation target. For mammalian cells, such promoters include the CMV promoter, as well as the SV40 late promoter and retroviral LTRs (long terminal repeat elements), although many other promoter elements well known to the art may be employed in the practice of the invention.

Other elements functional in the host cells, such as introns, enhancers, polyadenylation sequences and the like, may also be a part of the preselected DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

The recombinant DNA can be readily introduced into the host cells, e.g., mammalian, bacterial or insect cells, by transfection with an expression vector comprising DNA encoding a sterol methyltransferase or its complement, by any procedure useful for the introduction into a particular cell, e.g., physical or biological methods, to yield a transformed cell having the recombinant DNA stably integrated into its genome or having the recombinant DNA stably maintained as an extrachromosomal element (e.g., a plasmid), so that the DNA molecules, sequences, or segments, of the present invention are expressed by the host cell.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. The main advantage of physical methods is that they are not associated with pathological or oncogenic processes of viruses. However, they are less precise, often resulting in multiple copy insertions, random integration, disruption of foreign and endogenous gene sequences, and unpredictable expression. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like. For insect cells, baculovirus vectors are generally employed to introduce foreign genes to those cells.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian, bacterial or insect origin, but other cell lines or host cells may be employed, including plant, yeast or fungal cell sources.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding the sterol methyltransferase or its complement, which host cell may or may not express significant levels of autologous or "native" sterol methyltransferase.

To confirm the presence of the preselected DNA sequence in the host cell, a variety of assays may be performed. Such assays include, for example, "molecular biological" assays well known to those of skill in the art, such as Southern and Northern blotting, RT-PCR and PCR; and/or "biochemical" assays, such as detecting the presence or absence of sterol methyltransferase, e.g., by immunological means (ELISAs and Western blots) or enzymatic assays.

To detect and quantitate RNA produced from introduced preselected DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the protein product of the introduced preselected DNA sequence or evaluating the phenotypic changes brought about by the expression of the introduced preselected DNA segment in the host cell.

B. Polypeptides, Variants, and Derivatives Thereof of the Invention

The present isolated, purified *C. albicans* sterol methyltransferase polypeptides, variants or derivatives thereof, can be synthesized in vitro, e.g., by the solid phase peptide synthetic method or by recombinant DNA approaches which are well known to the art. The solid phase peptide synthetic method is an established and widely used method, which is described in the following references: Stewart et al., *Solid Phase Peptide Synthesis*, W. H. Freeman Co., San Francisco (1969); Merrifield, *J. Am. Chem. Soc.*, 85 2149 (1963); Meienhofer in "Hormonal Proteins and Peptides," ed.; C. H. Li, Vol. 2 (Academic Press, 1973), pp. 48–267; and Bavaay and Merrifield, "The Peptides," eds. E. Gross and F. Meienhofer, Vol. 2 (Academic Press, 1980) pp. 3–285. These peptides or polypeptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Purification of recombinant *C. albicans* sterol methyltransferase from the culture medium or the intact cells, if desired, may be achieved by conventional purification means such as ammonium sulfate precipitation, column chromatography, and the like, and fractions containing the *C. albicans* sterol methyltransferase polypeptide can be identified by, for example, enzymatic activity or Western blot analysis. Purification of a *C. albicans* sterol methyltransferase may be accomplished by methods such as those disclosed in Ator et al., 1989 and Ator et al., 1992.

Once isolated and characterized, derivatives, e.g., chemically derived derivatives, of a given *C. albicans* sterol methyltransferase polypeptide can be readily prepared. For example, amides of *C. albicans* sterol methyltransferase polypeptide or variants thereof may be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

Salts of carboxyl groups of a polypeptide or polypeptide variant of the invention may be prepared in the usual manner by contacting the polypeptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the C. albicans sterol methyltransferase polypeptide or polypeptide variants may be prepared by utilizing an N-acyl protected amino acid for the final condensation, or by acylating a protected or unprotected polypeptide. O-acyl derivatives may be prepared, for example, by acylation of a free hydroxy polypeptide or polypeptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the polypeptide or polypeptide variant. Other amino-terminal modifications include aminooxypentane modifications (see Simmons et al., Science, 276, 276 (1997)).

In addition, the amino acid sequence of C. albicans sterol methyltransferase can be modified so as to result in a C. albicans sterol methyltransferase variant. The modification includes the substitution of at least one amino acid residue in the polypeptide for another amino acid residue, including substitutions which utilize the D rather than L form, as well as other well known amino acid analogs. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citrulline, α-methyl-alanine, para-benzoyl-phenylalanine, phenylglycine, propargylglycine, sarcosine, and tert-butylglycine.

One or more of the residues of the polypeptide can be altered, preferably so long as the polypeptide variant is biologically active. For example, for C. albicans sterol methyltransferase variants, it is preferred that the variant has a similar, if not greater, biological activity than that of the corresponding non-variant wild type polypeptide, e.g., a polypeptide having SEQ ID NO:2. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/ alanine/threonine as hydrophilic amino acids.

Conservative substitutions are shown in FIG. 2 under the heading of exemplary substitutions. More preferred substitutions are under the heading of preferred substitutions. After the substitutions are introduced, the variants are screened for biological activity.

Amino acid substitutions falling within the scope of the invention, are, in general, accomplished by selecting substitutions that do not differ significantly in their effect on maintaining (a) the structure of the polypeptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic; trp, tyr, phe.

The invention also envisions polypeptide variants with non-conservative substitutions. Non-conservative substitutions entail exchanging a member of one of the classes described above for another.

Acid addition salts of the polypeptide or variant polypeptide or of amino residues of the polypeptide or variant polypeptide may be prepared by contacting the polypeptide or amine with one or more equivalents of the desired inorganic or organic acid, such as, for example, hydrochloric acid. Esters of carboxyl groups of the polypeptides may also be prepared by any of the usual methods known in the art.

The invention will be further described by the following example.

EXAMPLE I

Materials and Methods

Strains and plasmids. C. albicans CAI4 (Δura3::imm434/ Δura3::imm434) (Fonzi et al., 1993) was used for disruption of both copies of ERG6. S. cerevisiae erg6 deletion strain BKY48-5C (αleu2-3 ura3-52 erg6Δ::LEU2) was used as the recipient strain for transformation with the Candida genomic library (Goshorn et al., 1992). E. coli DH5Δ was used as the host strain for all plasmid constructions. Plasmid pRS316 was obtained from P. Heiter (Sikorski et al., 1989) and Bluescript plasmid was obtained from Stratagene (La Jolla, Calif.).

Media. CAI4 was grown on YPD complete medium containing 1% yeast extract (Difco), 2% Bacto-peptone (Difco) and 2% glucose. Complete synthetic medium (CSM) was used for transformation experiments and contained 0.67% yeast nitrogen base (Difco), 2% glucose and 0.8 g/l of a mixture of amino acids plus adenine and uracil (Bio101). CSM "drop out" media contained the above without uracil. Uridine was added at 80 mg/l. CSM media containing uridine and 5-fluoroorotic acid (5-FOA) at 1 g/l was used to regenerate the ura3 genetic marker as outlined by Fonzi et al. (1993). All experiments were carried out at 30° C. unless otherwise indicated.

Cloning of ERG6. Transformation of S. cerevisiae strain BKY48-5C using the Candida gene library was carried out according to a lithium acetate modified protocol developed by Gaber et al. (1989) for erg6 transformations. The C. albicans ERG6 gene was cloned by transforming a S. cerevisiae erg6 deletion strain (BKY485C) with a Candida genomic DNA library obtained from Dr. Stew Scherer (University of Minnesota) (Goshorn et al., 1992). The library contained Sau3A fragments of Candida genomic DNA ligated into the BamHI site of the 9.6 kb Candida-Saccharomyces shuttle vector, p1041. p1041 contains the C. albicans URA3 gene as a selectable marker and two origins of replication. One origin of replication is a portion of 2μ DNA that is required for plasmid replication in Saccharomyces and the other origin is a CARS sequence (Candida autonomously replicating sequence) that is required for replication in Candida. Additionally, this vector contains DNA sequences so as to permit plasmid replication in E. coli. Transformants containing Candida ERG6 DNA were subcloned into the Saccharomyces vector, pRS316, for complementation analyses and DNA sequencing. All Candida transformations for disruption experiments were carried out essentially according to procedures of Sanglard et al. (1996). Plasmid p5921, obtained from Fonzi et al. (1993), was the source of the ura blaster for Candida ERG6 disruption experiments.

Approximately 1250 transformants were obtained after plating potential transformants on a uracil dropout medium which ensures the presence of the plasmid. These transformants were then screened on 0.06 µg/ml cycloheximide. *S. cerevisiae* erg6 strains are nystatin resistant and cycloheximide sensitive. Transformants that were resistant to this level of cycloheximide (cyh$^r$) were further tested for the presence of intracellular ergosterol. Sterols extracted from *S. cerevisiae* erg6 and the transformants were analyzed by UV and GC/MS to confirm the sterol phenotypes.

DNA sequencing of the Candida ERG6 gene. The plasmid insert containing the ERG6 gene was sequenced in both directions using the Sanger dideoxy chain termination method. Initially T3 and T7 primers were used and as DNA sequence became available, primers were generated from sequenced DNA.

PCR. PCR analyses were used to verify disruptions of both Candida ERG6 genes. Primers P1, P2, and P3 were used to distinguish ERG6 disrupted genes on the basis of size. The primers correspond to ERG6 sequences. Primer 4 corresponds to sequences in the hisG region of the ura blaster. P1 has the sequence 5'-CACATGGGTGAAATTAG-3' (SEQ ID NO:6); P2 corresponds to 5'-CTCCAGTTCAATTAGCAG-3' (SEQ ID NO:7); P3 is 5'-TGTGCGTGTACAAAGCAC-3' (SEQ ID NO:8); and P4 is 5'-GATAATACCGAGATCGAC-3' (SEQ ID NO:9). PCR buffers and Taq polymerase were obtained from Promega. Buffer composition was 10 mM Tris-HCl (pH 9) and 2 mM $MgCl_2$ and reactions mixtures contained 0.2 mM dNTPs and 0.5 U of polymerase. Conditions for amplification were as follows: the first cycle of denaturation at 94° C. was for 5 minutes followed by 40 cycles of annealing at 50° C. for 2 minutes, elongation at 72° C. for 3 minutes, and denaturation at 94° C. for 1 minute. A final elongation step was performed at 72° C. for 20 minutes. Protocols for preparation of the Candida template DNA is described in Ausubel et al. (1995).

Sterol analyses. Sterols were isolated as non-saponifiables as described previously (Molzhan et al., 1972). UV analysis of sterols in extracts was accomplished by scanning from 200 to 300 nm using a Beckman DU 640 spectrophotometer. GC analyses of non-saponifiables were conducted on a HP5890 series II equipped with the HP chemstation software package. The capillary column (HP-5) was 15 m×0.25 mm×0.25 mm film thickness and was programmed from 195° C. to 300° C. (three minutes at 195° C., then an increase at 5.5° C./minute until the final temperature of 300° C. was reached and held for 4 minutes). The linear velocity was 30 cm/sec using nitrogen as the carrier gas and all injections were run in the splitless mode. GC/MS analyses were done using a Varian 3400 gas chromatograph interfaced to a Finnigan MAT SSQ 7000 mass spectrometer. The GC separations were done on a fused silica column, DB-5, 15 m×0.32 mm×0.25 mm film thickness programmed from 50° C. to 250° C. at 20° C./minute after a 1 minute hold at 50° C. The oven temperature was then held at 250° C. for 10 minutes before programming the temperature to 300° C. at an increase of 20° C./minute. Helium was the carrier gas with a linear velocity of 50 cm/second in the splitless mode. The mass spectrometer was in the electron impact ionization mode at an electron energy of 70 eV, an ion source temperature of 150° C., and scanning from 40 to 650 atomic mass units at 0.5 second intervals.

Drug susceptibility testing in *C. albicans*. Drug susceptibilities of *C. albicans* wild type and erg6 strains were conducted using cells harvested from overnight YPD plates grown at 37° C. Cells were suspended in YPD to a concentration of $1\times10^7$ ($OD_{660}$ of 0.5) cells per ml. Cells were plated by transferring 5 µl of the original suspension ($10^0$) plus $10^{-1}$ and $10^{-2}$ dilutions to YPD plates containing the drug to be tested. The plates were incubated for 48 hours at 37° C. and observed for growth.

Clotrimazole, brefeldin A, cerulenin, cycloheximide, nystatin, and fluphenazine were obtained from Sigma Chemical Co. (St. Louis, Mo.), and ketoconazole from ICN (Costa Mesa, Calif.). Fenpropiomorph and tridemorph were obtained from Crescent Chemical Co., Hauppage, N.Y. Terbinafine is available from Sandoz.

Stock solutions of terbinafine, tridemorph, brefeldin A, and cerulenin were prepared in ethanol. Clotrimazole, ketoconazole, and fenpropiomorph stocks were prepared in dimethyl sulfoxide and fluphenazine and cycloheximide stocks were prepared in water. Nystatin was dissolved in N,N-dimethyl formamide (Sigma).

Nucleotide sequence accession numbers. GenBank accession numbers for the nucleotide sequences of ERG6 from *S. cerevisiae*, *A. thaliana*, and *T. ativum* are X74249 (SEQ ID NO:3), X89867 (SEQ ID NO:4), and U60755 (SEQ ID NO:5), respectively.

Results

Cloning of the *C. albicans* ERG6 gene. Four *S. cerevisiae* erg6 transformants which grew on cycloheximide were analyzed for sterol content. erg6 mutants which fail to synthesize ergosterol due to defects in the C-24 transmethylase gene accumulate principally zymosterol, cholesta-5,7, 24-trien-3β-ol and cholesta-5,7,22,24-tetraen-3β-ol (Molzhan et al., 1972). UV scans of the sterols obtained from a Saccharomyces erg6 strain as well as an erg6 transformant containing the Candida ERG6 gene are shown in FIG. 3. Sterols giving the erg6 spectrum contain absorption maxima at 262, 271, 282, and 293 nm as well as maxima at 230 and 238 nm. The latter two absorption maxima are due to conjugated double bonds which occur in the sterol side chain (cholesta-5,7,22,24-tetra-en-3β-ol). The ERG6 transformed strain does not have a conjugated double bond in the side-chain and gives absorption maxima only at 262, 271, 282, and 293 nm. The remaining three transformants yielded similar profiles. Gas chromatographic analysis of the erg6 mutant and the ERG6 transformants confirmed the presence of ergosterol in the latter strains. These results were also confirmed by mass spectrometry.

Figure 4:
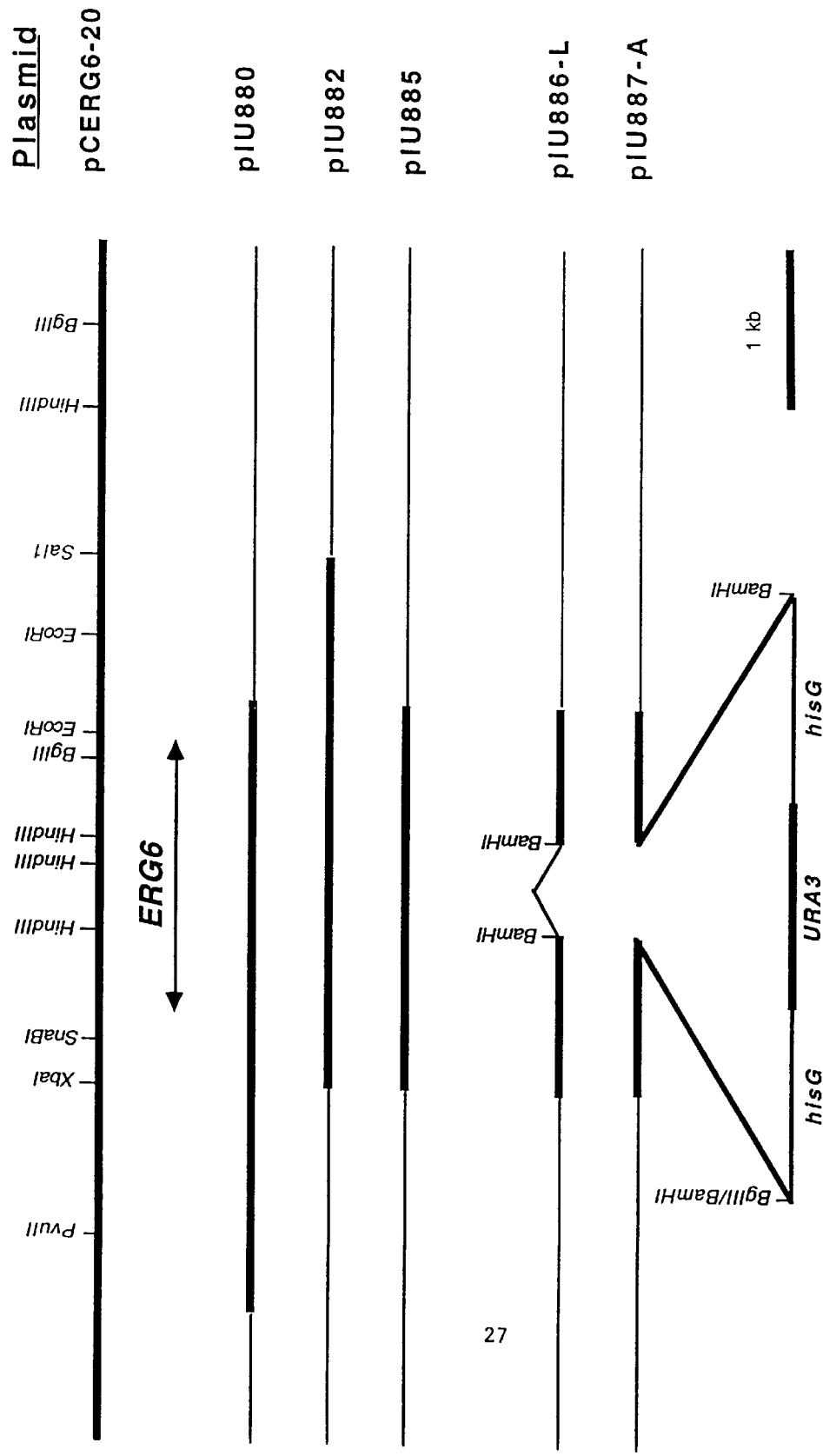
FIG. 4. A schematic representation of a *Candida albicans* ERG6 genomic clone (pCERG6-20) and three complementing subclones, pIU880, pIU882, and pIU885. Selected restriction endonuclease sites are shown. A subclone in which a 0.7 kb HindIII fragment within pIU885 was deleted, the cohesive ends filled in, and BamHI linkers (pIU886-L) added is shown. The insertion of the ura blaster into the BamHI site of pIU886-L resulted in pIU887-A.

Of the four transformants that restored the ability of the erg6 mutant to synthesize ergosterol, two of the transformants had an insert size of 8 kb (e.g., pCERG6-20; FIG. 4) and the other two had an insert of 14 kb (e.g., pCERG6-9). The pCERG6-9 insert contained the entire 8 kb DNA fragment of pCERG6-20, suggesting that the ERG6 gene resided within the 8 kb fragment. Growth of ergosterol producing transformants on media containing 5-FOA resulted in loss of the transforming plasmid. The loss of the plasmid restored the erg6 phenotype, which indicated that ergosterol production of the pCERG6-20 and pCERG6-9 transformants was plasmid mediated.

In order to locate the ERG6 gene within the plasmid insert, an approximately 4 kb subclone of the left arm of pCERG6-20 was inserted into the Saccharomyces vector pRS316 yielding plasmid pIU880 (FIG. 4). pIU880 was able to complement erg6. Plasmid pIU882, which contains a 2.4 kb overlap with pIU880, also complemented erg6 suggesting that the Candida ERG6 gene lies within this 2.4 kb fragment. This 2.4 kb fragment was subcloned into pRS316 by digesting pIU880 with XbaI-EcoRI to yield pIU885.

Figure 5:
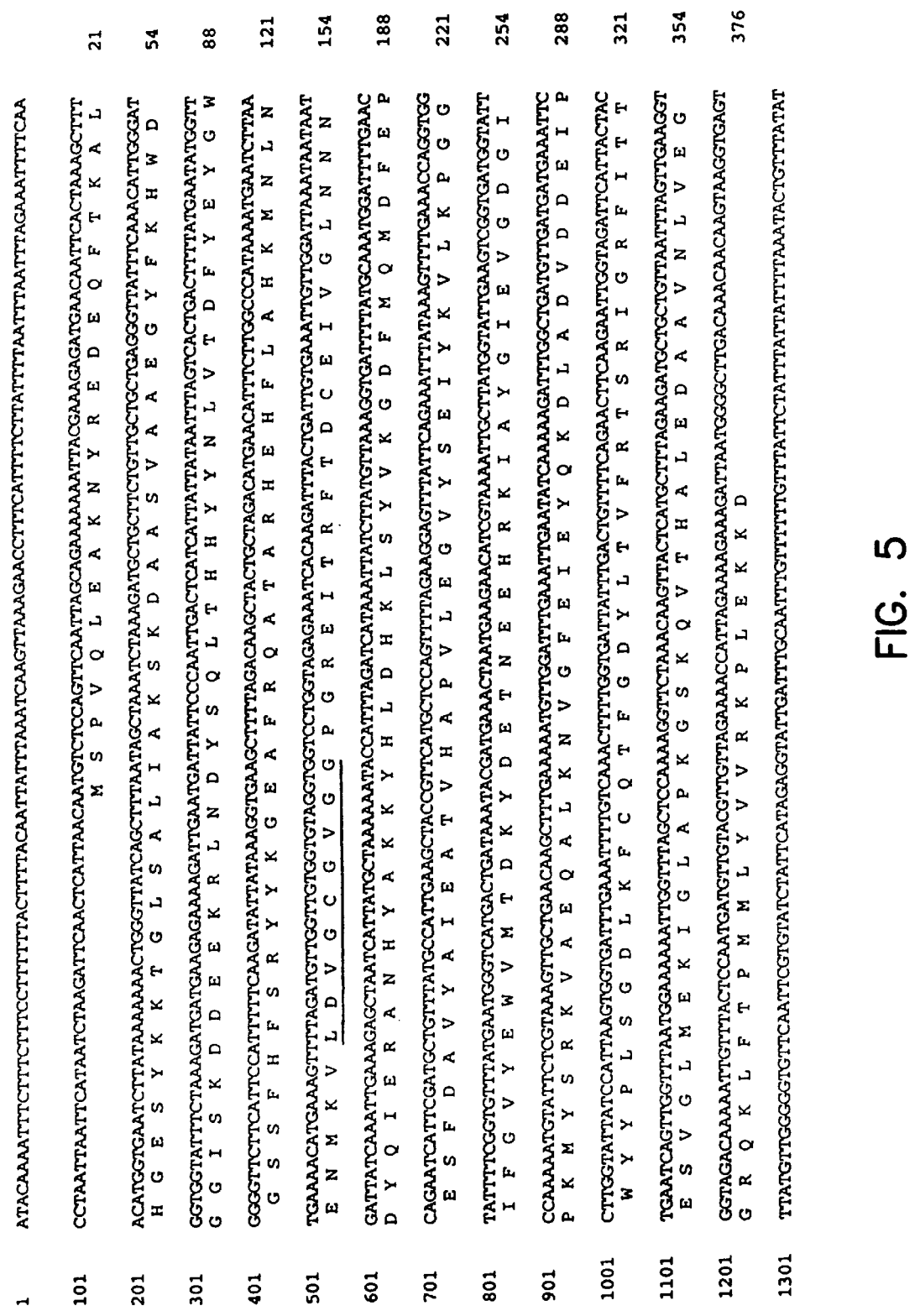

DNA sequencing of the Candida ERG6 gene. The 2.4 kb XbaI-EcoRI fragment was sequenced. The DNA sequence of this fragment and its corresponding amino acid sequence are shown in FIG. 5 (SEQ ID NO:1 and SEQ ID NO:2, respectively). The Candida ERG6 gene encodes a sterol methyltransferase which contains 377 amino acids and is 66% identical to the Saccharomyces counterpart. FIG. 6 shows an alignment between the Candida, Saccharomyces, Arabidopsis, and Triticum sterol methyltransferases. The percent identity of the Candida sterol methyltransferase to the Arabidopsis and Triticum sterol methyltransferase are 40% and 49%, respectively. A nine amino acid region (FIG. 6; amino acids 127–135 in the C. albicans sequence) represents the highly conserved S-adenosyl methionine binding site (Bouvier-Nave et al., 1997).

Creation of a C. albicans ERG6 heterozygote. Disruption of the Candida ERG6 gene to derive a sterol methyltransferase deficient strain was made more difficult since Candida, unlike Saccharomyces, is an obligate diploid and, thus, both copies of the ERG6 gene must be disrupted. To accomplish this, the "ura blaster" system developed by Fonzi et al. (1993) was employed. The ura blaster contains about 3.8 kb of repeat elements of hisG (derived from Salmonella) which flank the Candida URA3 gene. The plasmid pIU887-A containing the ura blaster inserted into the ERG6 gene is shown in FIG. 4. The 2.4 kb XbaI-EcoRI ERG6 DNA fragment was cloned into the pBluescript vector-KS(+) in which a HindIII site was filled in with the Klenow fragment of DNA polymerase I, yielding pIU886. pIU886-L was subsequently derived by deleting a 0.7 kb HindIII fragment within the ERG6 coding sequence, filling in this site with Klenow followed by the addition of BamHI linkers. p5921, containing the ura blaster, was digested with SnaBI and StuI, followed by religation, which resulted in a deletion of 6 bp in one of the hisG regions and destruction of these two sites. The modified p5921 was then digested with BamHI and BglII to release the 3.8 kb ura blaster which was then ligated into pIU886-L that had been digested with BamHI to generate pIU887-A.

Candida strain CAI4 was transformed with the 5.3 kb BglII-SnaBI fragment containing the ura blaster and ERG6 flanking recombinogenic ends of 0.8 and 0.9 kb. Transformants containing the single disrupted ERG6 allele resulting in heterozygosity for ERG6 were confirmed using PCR after selection for loss of the URA3-hisG region. Intrachromosomal recombination between the linear hisG sequences resulted in loss of one of the hisG repeats and the URA3 thus permitting reuse of the ura blaster for the subsequent disruption of the ERG6 gene on the homologous chromosome. Selection for colonies on 5-FOA resulted in growth of only uridine requiring strains (Boeke et al., 1987).

Creation of C. albicans erg6 strains. The creation of a Candida erg6 mutant strain in which both alleles were disrupted was accomplished in two different ways. The ERG6 heterozygote was placed onto plates containing high concentrations of nystatin (15 μg/ml) and after 3 days nystatin resistant colonies appeared. When colony purified, these resistant colonies were found to be erg6 homozygotes that resulted from mitotic recombination. A second method used to generate erg6 homozygotes was to transform the ERG6 heterozygote with the ura blaster. Two kinds of transformants were obtained: wild type and slow growing colonies. Both types of colonies were tested for resistance to nystatin and only the slower growing colonies were nystatin resistant.

Figure 7:
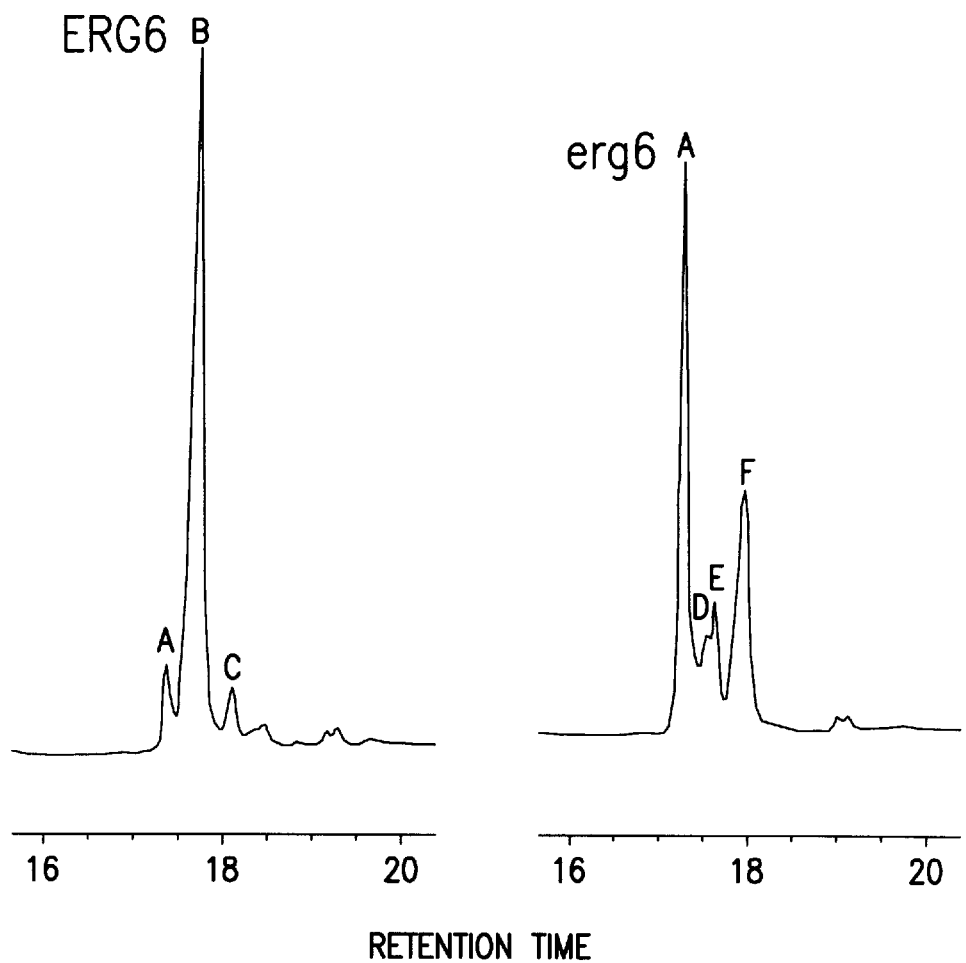
FIG. 7. Gas chromatography of the sterols of the wild type and an erg6 strain of *Candida albicans*. Peak A; zymosterol, Peak B; ergosterol, Peak C; fecosterol, Peak D; cholesta-5,7,24-trien-3β-ol, Peak E; cholesta-7,24-dien-3β-ol, Peak F; cholesta-5,7,22,24tetraen-3β-ol.

Confirmation of erg6 homozygosity by sterol analyses. The sterols isolated from wild type and putative erg6 homozygotes were analyzed by UV spectrophotometry and gas-chromatography/mass spectroscopy. All of the putative erg6 homozygotes contained erg6-like UV scans similar to the S. cerevisiae erg6 scan shown in FIG. 3. Additionally, GC/MS of erg6 mutant sterols confirmed that only cholesterol-like (C27) sterols accumulate since the side-chain cannot be methylated. FIG. 7 represents a GC profile demonstrating that the putative erg6 mutants accumulate C-27 sterols and are deficient in side-chain transmethylation. Whereas the predominant sterol in the CAI4 wild type is ergosterol (peak B, 76%), the principal sterols in erg6 mutants are: zymosterol (peak A, 43%), cholesta-5,7,24-trien-3β-ol (peak D, 6%) cholesta-7,24-dien-3β-ol (peak E, 9%), and cholesta-5,7,22,24-tetraen-3β-ol (peak F, 29%).

Figure 8A:
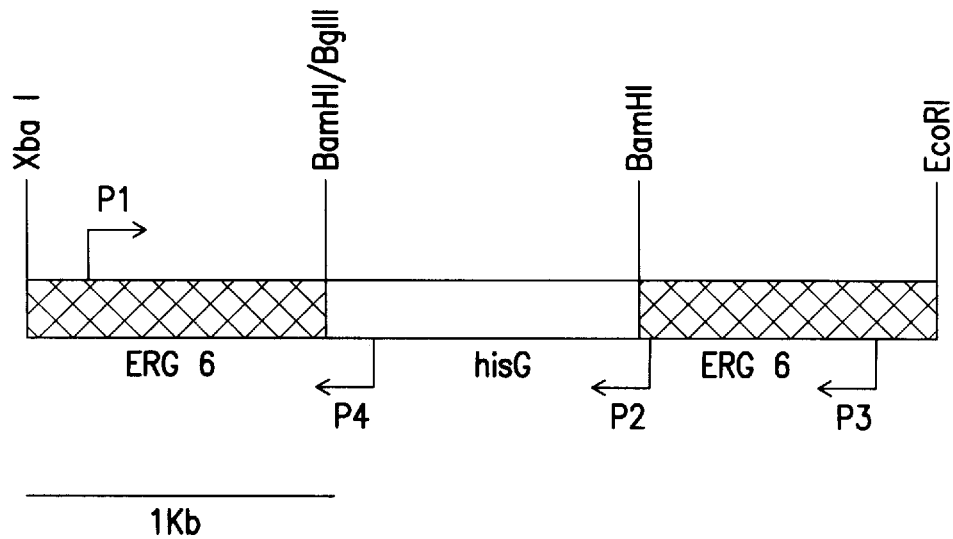
FIG. 8. (A). A schematic representation of the ura blaster disruption of the ERG6 gene. The location and orientation of PCR primers is shown ("P2", "P3", and "P4"). (B). Agarose gel electrophoretic confirmation of heterozygote and homozygote disruptants of the ERG6 gene. CAI4 (wild type), lanes 1 and 2; CAI4-6-5 (heterozygote), lanes 3 and 4; 5AB-15 (homozygote derived from ura blaster transformation followed by mitotic recombination), lanes 5 and 6; HO11-A3 (homozygote derived from two rounds of ura blaster transformation), lanes 7 and 8. The image was captured on disc and the photograph generated using Photoshop on MacIntosh.
Figure 8B:
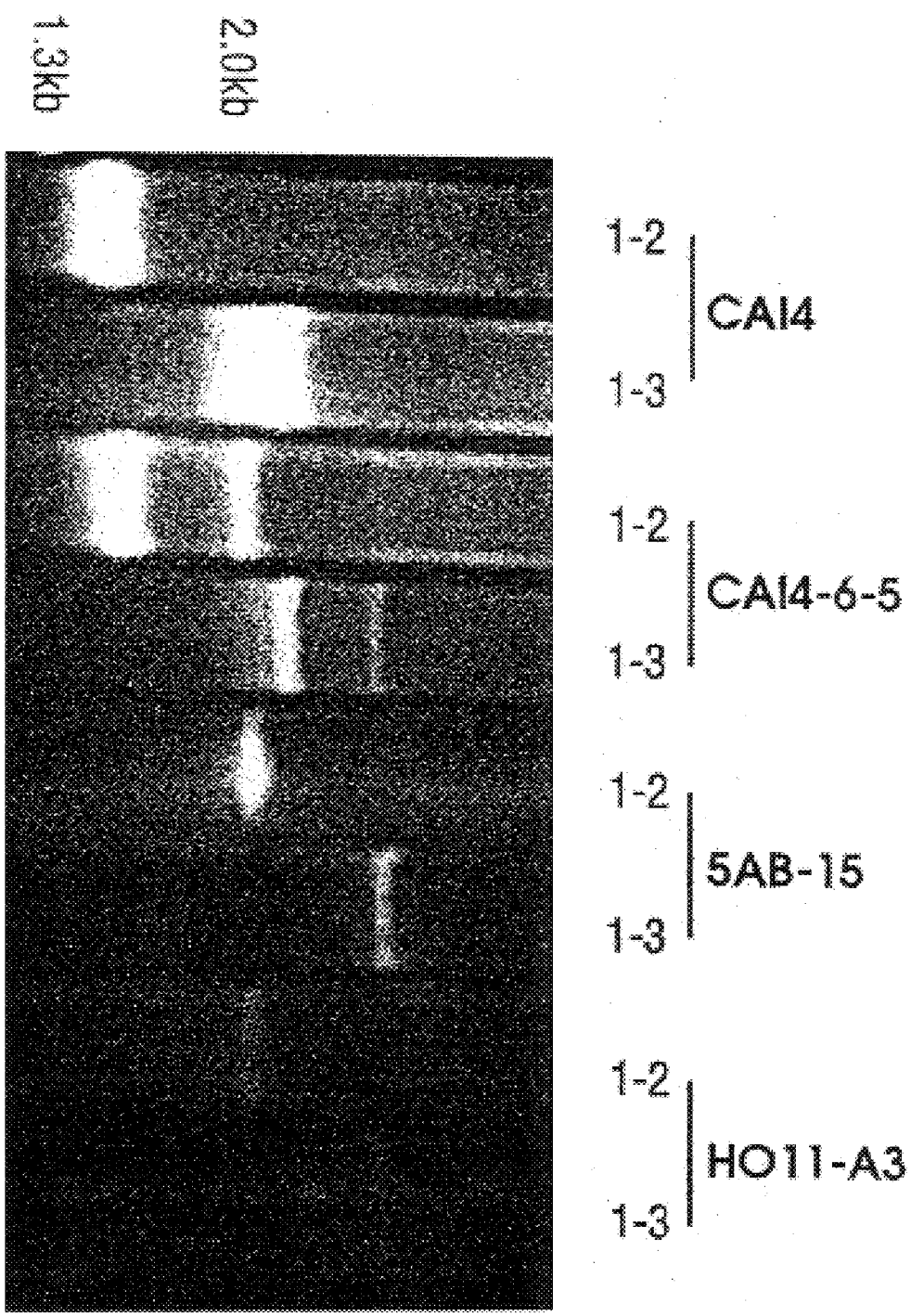

PCR confirmation of homozygous disruptions. Confirmation of the disruption of both copies of the C. albicans ERG6 gene by mitotic recombination of the heterozygote and by a second transformation using the ura blaster was performed by employing four PCR primers. The ura blaster containing a 3.8 kb region of hisG-URA3-hisG replaced the 0.7 kb of ERG6 DNA (FIG. 8A). This was followed by deletion of the hisG-URA3 sequence such that in effect the remaining 1.2 kb hisG sequence replaced a 0.7 kb ERG6 deletion. The expected PCR amplification product of CAI4 using P1-P2 or P1-P3 was observed, i.e., a product of 1.5 kb and 2.15 kb, respectively (FIG. 8B, lanes 1 and 2). The product from amplification of the heterozygote CAI-4-6-5 with P1-P2 was 1.5 kb (wild type allele) and 2.01 kb (disrupted ERG6 allele). The product from amplification of CAI-4-6-5 with P1-P3 primers was 2.15 kb (wild type) and 2.65 kb (disrupted ERG6) (FIG. 8B, lanes 3 and 4). Primer pair P1-P4 gives a 1.1 kb band demonstrating the presence of hisG within the ERG6 sequence. The erg6 homozygotes, 5AB15, obtained by mitotic recombination, and HO11-A3, obtained by ura blaster transformation, yielded identical amplification products using primers P1-P2 (2.01 kb) and primers P1-P3 (2.65 kb), as shown in FIG. 8B, lanes 5–8.

Figure 9:
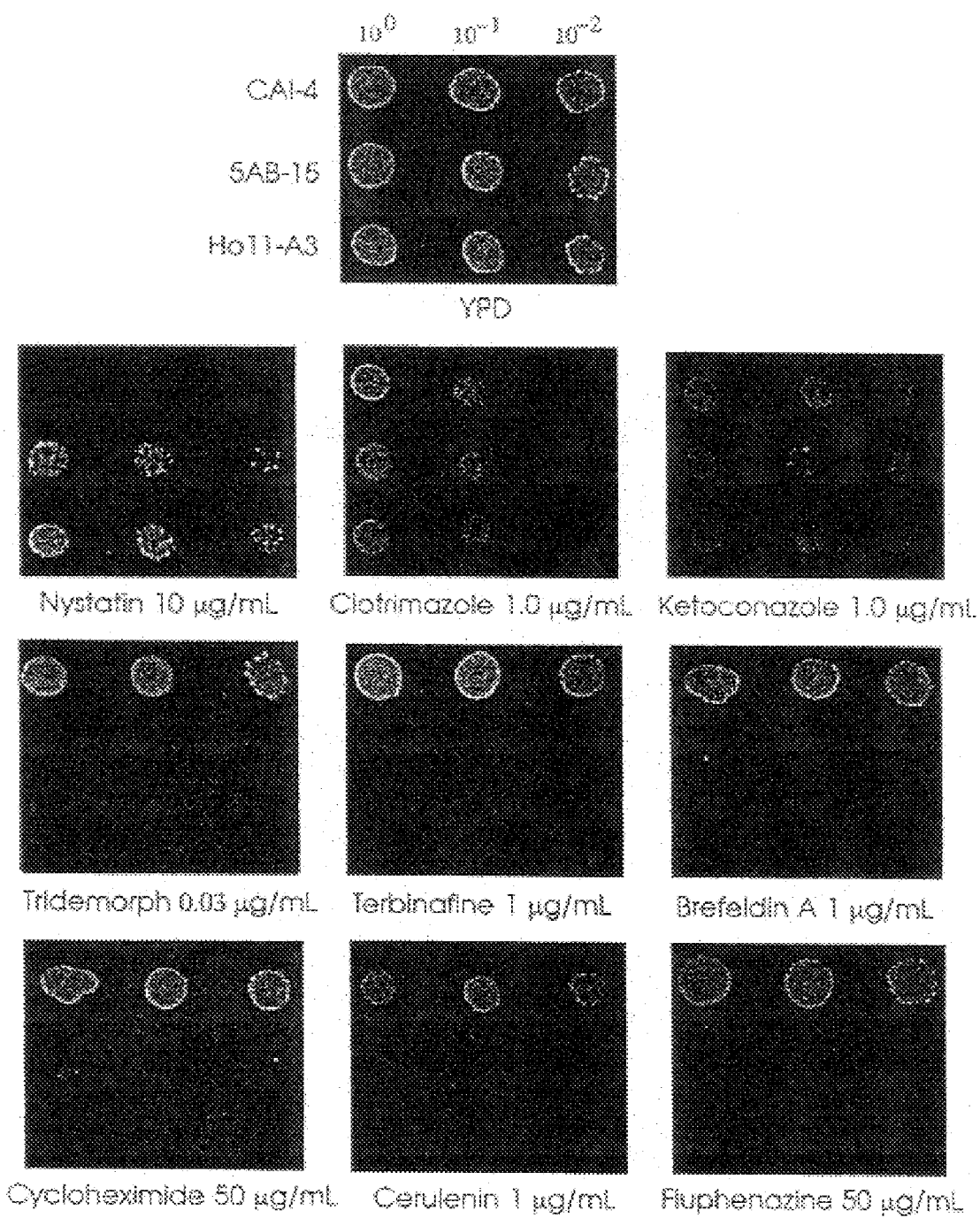
FIG. 9. Growth responses of wild type (CAI4), homozygous erg6 derived from ura blaster transformation (5AB-15) and homozygous erg6 derived from mitotic recombination (HO11-A3) in the presence of sterol biosynthesis inhibitors and metabolic inhibitors. Cells were grown at 37° C. to a density of $1\times10^7$ cells/ml and 5 μl inoculated at $10^0$, $10^{-1}$, and $10^{-2}$ dilutions. The image was captured on disc and the photograph generated using Photoshop on MacIntosh.

Drug susceptibilities of C. albicans erg6 strains. The susceptibilities of the erg6 strains as compared to wild type C. albicans were determined using a number of antifungal compounds and general cellular inhibitors (FIG. 9). The erg6 strains were shown to be more resistant to nystatin while showing near identical sensitivity to the azole antifungals, clotrimazole and ketoconazole. Significantly increased susceptibilities of the erg6 strains were noted for tridemorph and fenpropiomorph, inhibitors of sterol Δ14-reductase and Δ8-Δ7 isomerase (Baloch et al., 1984); terbinafine, an allylamine antifungal inhibiting squalene epoxidase (Jandrositz et al., 1991); brefeldin A, an inhibitor of Golgi function (Venkateswarlu et al., 1997); cycloheximide, a common protein synthesis inhibitor; cerulenin, an inhibitor of fatty acid synthesis (Monsaki et al., 1993); and fluphenazine, a compound which interferes with the function of calmodulin (Hait et al., 1993).

TABLE 1

Drug susceptibilities[a] of ERG6 and erg6 strains of C. albicans to antifungal agents and metabolic inhibitors.

| DRUG | ERG6 | erg6 |
| --- | --- | --- |
| Nystatin | 2.5 | 15 |
| Clotrimazole | 1 | 1 |
| Ketoconazole | 5 | 5 |
| Terbinafine | >50 | 1 |

TABLE 1-continued

Drug susceptibilities[a] of ERG6 and erg6 strains of *C. albicans* to antifungal agents and metabolic inhibitors.

| DRUG | ERG6 | erg6 |
|---|---|---|
| Fenpropiomorph | 0.5 | 0.005 |
| Tridemorph | >90 | 0.03 |
| Brefeldin A | 50 | 1 |
| Cerulenin | 2 | 1 |
| Cycloheximide | >600 | 50 |
| Fluphenazine | 100 | 50 |

[a]denotes inhibitor concentration ($\mu$g/ml) at which no growth appeared after 48 hours under the growth conditions described in the brief description of FIG. 9.

The determination of drug concentrations sufficient to completely inhibit growth on plates yielded the data shown in Table 1. The concentration (2.5 $\mu$g/ml) of nystatin required for complete inhibition of wild type is within the normal range for a wild type strain (Molzhan et al., 1972) while the erg6 mutants showed a resistance level similar to that noted for erg6 mutants of *S. cerevisiae* (Molzhan et al., 1972). As demonstrated on plates (FIG. 9), the azoles show equal efficacy against both wild type and erg6 strains. In contrast, the erg6 mutants show significantly increased susceptibilities to other antifungals and metabolic inhibitors. Erg6 susceptibilities to cerulenin and fluphenazine showed two-fold increases while those for terbinafine and brefeldin A were about 50 times greater than for wild type. Cycloheximide susceptibility increased about eleven-fold while the greatest increases in susceptibility increase was shown for the morpholines, fenpropiomorph (100-fold) and tridemorph (several thousand-fold).

Discussion

Candida erg6 mutants are of interest as the permeability of these mutants might make them more sensitive to known and new antifungals or even make them sensitive to compounds previously found not to be effective when ergosterol is present in the cell. Using a Candida genomic library, Candida ERG6 was isolated by complementing an erg6 mutant of Saccharomyces. To further identify the ERG6 gene for sensitivity to nystatin and resistance to cycloheximide were also employed in conjunction with the complementation assay. Nystatin functions by binding to membrane ergosterol and causing cell leakage which leads to cell death (Brajtburg et al., 1990). Mutants such as erg6 do not produce ergosterol and utilize sterol intermediates in place of membrane ergosterol. Nystatin has lower affinity for sterol intermediates thus leading to resistance in non-ergosterol containing strains. Expression of the Candida ERG6 gene in Saccharomyces erg6 mutants restores the nystatin-sensitive phenotype. The ERG6 gene also elevates the cell permeability barrier to normal levels, thus conferring cycloheximide resistance at low drug concentrations. Cloning of the Candida ERG6 gene was also confirmed by UV analysis of sterol composition and GC/MS analysis of accumulated sterols in Saccharomyces erg6 and transformed strains containing the Candida ERG6 gene. Final confirmation that the ERG6 had been obtained was provided by sequencing of the Candida ERG6.

To determine whether the ERG6 gene in Candida was essential for viability, the two copies of the gene were disrupted by first creating a heterozygote using the ura blaster disruption protocol. The second copy of the ERG6 gene was disrupted by either allowing for mitotic recombination or by a second disruption with the ura blaster. In both cases the resulting erg6 homozygotes were viable, indicating that the ERG6 gene in *C. albicans* is not essential for viability. Both types of erg6 mutants were confirmed by both sterol analysis and PCR analysis of the disruptions.

With the continued increase in resistance to the azole antifungals, new approaches to antifungal chemotherapy are strongly indicated. One approach is to disarm the resistance mechanism. A primary mechanism in *C. albicans* for azole resistance is the increase in expression of efflux systems which utilize the azoles as substrates. Both the ABC (ATP-binding cassette) transporter gene CDR1 and a gene (BEN[r]) belonging to a major facilitator multidrug transporter have been implicated in this process (Sanglard et al., 1995). A report by Sanglard et al. (1996) has shown that disruption of the CDR1 gene results in a cell that showed increased susceptibilities to the azole, allylamine, and morpholine antifungals as well as other metabolic inhibitors including cycloheximide, brefeldin A, and fluphenazine. Although not effective alone, disruptions of BEN[r] were shown to work synergistically with CDR1 with two metabolic inhibitors. The CDR1 system can provide for an assay for drugs not subject to efflux by these transporters and could also be used to select for compounds which could block the action of the transporters directly. Such approaches would avoid or disarm resistance mechanisms, respectively.

The testing of Candida erg6 mutants for their susceptibility to antifungal and metabolic inhibitors indicated that these mutants had increased sensitivity to a wide variety of compounds. Azoles were an exception in that they show no difference in efficacy between wild type and mutant strains. Apparently, the permeability changes are unrelated to the entry mechanism for these compounds. The remainder of the compounds tested, including two other antifungal compounds with different mechanisms of action, showed significantly increased efficacy in the erg6 strain.

These findings have important applicability from several perspectives. First, the availability of the *C. albicans* ERG6 gene allows it to be used as a screen for the identification of inhibitory compounds that specifically target the ERG6 gene product. This approach has been successfully utilized in cloning of one of the HMGCoA reductase genes (Rine et al., 1983) as well as the ERG11 (Kalb et al., 1986) and ERG24 (Marcireaux et al., 1992) genes. In applying this strategy for the purpose of identifying ERG6 gene product inhibitors, the sensitivity of a wild type strain would be compared to that of a strain carrying additional copies of ERG6 on a high copy number plasmid. Inhibition of the wild type but not the multiple copy strain would identify inhibition specific to the sterol methyltransferase. Treatment of a fungal pathogen with such an inhibitor would result in a metabolically compromised cell that would be more susceptible to existing antifungals and metabolic inhibitors.

Second, the results predict that an inhibitor of the ERG6 gene product would result in a fungal organism that is hypersensitive to known compounds or new compounds to which the cell is normally impermeable. Treatment of a cell with both inhibitors would thus produce a synergistic effect. Synergism has been shown (Barrett-Bee et al., 1995) using the experimental sterol methyltransferase inhibitor, ZM59620, in tandem with allylamine and morpholine antifungals. In these studies, the concentrations of the drugs in the combined treatment were significantly below the individual concentrations necessary for both the inhibition of ergosterol biosynthesis and growth inhibition. Thus, because of the increased drug access produced by inhibitors of the sterol methyltransferase, other inhibitors can be clinically employed at reduced dosages.

The erg6 system also allows for the replacement of in vitro testing of inhibitors by utilizing the increased permeability characteristics inherent in the in vivo mutant system. This allows characterization of potential inhibitors that normally fail to reach intracellular targets due to a lack of permeability.

Since the erg6 system results in a compromised cell which is highly permeable to a variety of compounds and since selection of new inhibitors using high copy number ERG6 plasmids allows for easy identification, this system has superior potential for the development of new antifungal treatment protocols.

REFERENCES

Ator, M. A., S. J. Schmidt, J. L. Adams and R. E. Dolle. 1989. Mechanism and inhibition of $\Delta^{24}$-sterol methyltransferase from *Candida albicans* and *Candida tropicalis*. *Biochemistry*, 28, 9633–9640.

Ator, M. A., S. J. Schmidt, J. L. Adams, R. E. Dolle, L. I. Kruse, C. C. Frey and J. M. Barone. 1992. Synthesis, specificity and antifungal activity of inhibitors of the *Candida albicans* $\Delta^{24}$-sterol methyltransferase. *J. Med. Chem.*, 35, 100–106.

Ausubel, F., R. Brent, R. E. Kingston, D. D. Moore, J. G. Seidman, J. A. Smith, and K. Struhl (eds.) 1995. *Short Protocols in Molecular Biology*, Third Ed.

Baloch, R. I., E. L. Mercer, T. E. Wiggins, and B. C. Baldwin. 1984. Inhibition of ergosterol biosynthesis in *Saccharomyces cerevisiae* and *Ustilago maydis* by tridemorph, fenpropiomorph, and fenpropidin. *Phytochemistry* 23:2219–2226.

Bard, M., N. D. Lees, L. A. Burrows, and F. W. Kleinhans. 1978. Differences in crystal violet dye uptake and cation-induced death among yeast sterol mutants. *J. Bacteriol.* 135:1146–1148.

Barrett-Bee, K., and G. Dixon. 1995. Ergosterol biosynthesis inhibition: a target for antifungal agents. *Acta Biochim. Polon* 42:465–480.

Boeke, J. D., J. Truehart, G. Natsoulis, and G. R. Fink. 1987. 5-Fluoro-oroticacid as a selective agent in yeast molecular genetics. *Meth Enzymol.* 154:164–175.

Bouvier-Navé, P., T. Husselstein, T. Desprez, and P. Benveniste. 1997. Identification of cDNAs encoding sterol methyl transferases involved in the second methylation step of plant sterol biosynthesis. *Eur. J. Biochem.* 246:518–529.

Brajtburg, J., W. G. Powderley, G. S. Kobayashi, and G. Medoff. 1990. Amphotericin B: current understanding of mechanism of action. *Antimicrob. Agents Chemother.* 34:183–188.

Clark, F. S., T. Parkinson, C. A. Hitchcock, and N. A. R. Gow. 1996. Correlation between rhodamine 123 accumulation and azole sensitivity in Candida species: possible role for drug efflux in drug resistance. *Antimicrob. Agents Chemother.* 40:419–425.

Denning, D. W., K. Venkateswarlu, K. L. Oakley, M. J. Anderson, N. J. Manning, D. A. Stevens, D. W. Warnock, and S. L. Kelly. 1997. Itraconazole resistance in *Aspergillus fumigatus*. *Antimicrob. Agents Chemother* 41:1364–1368.

Fonzi, W. A., and M. Y. Irwin. 1993. Isogenic strain construction and gene mapping in *Candida albicans*. *Genetics* 134:717–728.

Gaber, R. F., D. M. Copple, B. K. Kennedy, M. Vidal, and M. Bard. 1989. The yeast gene ERG6 is required for normal membrane function but is not essential for biosynthesis of the cell-cycle sparking sterol. *Mol. Cell Biol.* 9:3447–3456.

Georgopapadakou, N. H., and T. J. Walsh. 1994. Human mycoses: drugs and targets for emerging pathogens. *Science* 264:371–373.

Goshorn, A. K., S. M. Grindle, and S. Scherer. 1992. Gene isolation by complementation in *Candida albicans* and applications to physical and genetic mapping. *Infect. Immun.* 60:876–884.

Hait, W. N., J. F. Gesmonde, J. S. Lazo. 1993. Effect of anti-calmodulin drugs on the growth and sensitivity of C6 rat glioma cells bleomycin. *Anticancer Res.* 14:1711–1721.

Hebeka, E. K., and M. Solotorovsky. 1965. Development of resistance to polyene antibiotics in *Candida albicans*. *J. Bacteriol.* 89:1533–1539.

Jandrositz, A., F. Turnowski, and G Hogenaur. 1991. The gene encoding squalene epoxidase from *Saccharomyces cerevisiae*: cloning and characterization. *Gene* 107:155–160.

Kalb, V. F., J. C. Loper, C. R. Dey, C. W. Woods, and T. R. Sutter. 1986. Isolation of a cytochrome P-450 gene from *Saccharomyces cerevisiae*. *Gene* 45:237–245.

Kleinhans, F. W., N. D. Lees, M. Bard, R. A. Haak, and R. A. Woods. 1979. ESR determination of membrane permeability in a yeast sterol mutant. *Chem. Phys. Lipids* 23:143–154.

Lamb, D. C., B. C. Baldwin, K. J. Kwon-Chung, and S. L. Kelly. 1997. Stereoselective interaction of the azole antifungal agent SCH39304 with the cytochrome P-450 monooxygenase system isolated from *Cryptococcus neoformans*. *Antimicrob. Agents Chemother.* 41:1465–1467.

Lees, N. D., M. Bard, M. D. Kemple, R. A. Haak, R. and F. W. Kleinhans. 1979. ESR determination of membrane order parameter in yeast sterol mutants. *Biochim. Biophys. Acta* 553:469–475.

Lees, N. D., S. L. Lofton, R. A. Woods, and M. Bard. 1980. The effects of varies energy source and detergent on the growth of sterol mutants of *Saccharomyces cerevisiae*. *J. Gen. Microbiol.* 118:209–214.

Marcireaux, D., D. Guyonnet, and F. Karst. 1992. Construction and growth properties of a yeast strain defective in sterol 14-reductase. *Curr. Genet.* 22:267–272.

Mercer, E. I. 1993. Inhibitors of sterol biosynthesis and their applications. In: *Progress in Lipid Research*, Sprecher H. and J. L. Harwood (eds.), Pergamon Press, N.Y., pp. 357–416.

Molzhan, S. W., and R. A. Woods 1972. Polyene resistance and the isolation of sterol mutants in *Saccharomyces cerevisiae*. *J. Gen. Microbiol.* 72:339–348.

Monsaki, N., H. Funabashi, R. Shimazawa, J. Furukawa, A. Kawaguchi, S. Okuda, and S. Iwasaki. 1993. Effect of side-chain structure on inhibition of yeast fatty acid synthase by cerulenin analogues. *Eur. J. Biochem.* 211:111–115.

Moran, G. P., D. J. Sullivan, M. C. Henman, C. E. McCreary, B. J. Harrington, D. B. Shanley, and D. C. Coleman. 1997. Antifungal drug susceptibilities of oral *Candida dubliniensis* isolates from human immunodeficiency virus (HIV)-infected and non-HIV-infected subjects and generation of stable fluconazole-resistant derivatives in vitro. *Antimicrob. Agents Chemother.* 41:617–623.

Parkinson, T., D. J. Falconer, and C. A. Hitchcock. 1995. Fluconazole resistance due to energy-dependent drug efflux in *Candida glabrata*. *Antimicrob. Agents Chemother.* 39:1696–1699.

Pinto, W. J., and W. D. Nes. 1983. Stereochemical specificity for sterols in *Saccharomyces cerevisiae*. *J. Biol. Chem.* 258:4472–4476.

Powderley, W. G., G. S. Kobayashi, G. P. Herzig, and G. Medoff. 1988. Amphotericin B-resistant yeast infection in severely immunocompromised patients. *Amer. J. Med.* 84:826–832.

Rine, J., W. Hansen, E. Hardeman, and R. W. Davis. 1983. Targeted selection of recombinant clones through gene dosage effects. *Proc. Natl. Acad. Sci. USA* 80:6750–6754.

Sanglard, D., F. Ischer, M. Monod, and J. Bille. 1996. Susceptibilities of *Candida albicans* multidrug transporter mutants to various antifungal agents and other metabolic inhibitors. *Antimicrob. Agents Chemother.* 40:2300–2305.

Sanglard, D., K. Kuchler, F. Ischer, J. L. Pagani, M. Monod, and J. Bille. 1995. Mechanisms of resistance to azole antifungal agents in *Candida albicans* isolates from AIDS patients involve specific multidrug transporters. *Antimicrob. Agents Chemother.* 39:2378–2386.

Sikorski, R. S. and Hieter, P. 1989. A system of shuttle vectors and yeast host strains designed for efficient manipulation of DNA in *Saccharomyces cerevisiae*. *Genetics* 122:19–27.

Vanden Bossche, H., G. Willemsens, and P. Marichal. 1987. Anti-Candida drugs the biochemical basis for their activity. *Crit. Rev. Microbiol.* 15:57–72.

Venkateswarlu, K., M. Taylor, N. J. Manning, M. G. Rinaldi, and S. L. Kelly. 1997. Fluconazole tolerance in clinical isolates of *Cryptococcus neoformans*. *Antimicrob. Agents Chemother.* 41:748–751.

Vogel, J. P., J. N. Lee, D. R. Kirsch, M. D. Rose, and E. S. Sztul. 1993. Brefeldin A causes a defect in secretion in *Saccharomyces cerevisiae*. *J. Biol. Chem.* 268:3040–3043.

Welihinda, A. A., A. D. Beavis, and R. J. Trumbly. 1994. Mutations in LIS1 (ERG6) gene confer increased sodium and lithium uptake in *Saccharomyces cerevisiae*. *Biochim. Biophys. Acta* 1193:107–117.

Wheat, J., P. Marichal, H. Vanden Bossche, A. Le Monte, and P. Connolly. 1997. Hypothesis on the mechanism of resistance to fluconazole in *Histoplasma capsulatum*. *Antimicrob. Agents Chemother.* 41:410–414.

White, T. 1997a. Increased MRNA levels of ERG16, CDR, and MDRI correlate with increases in azole resistance in *Candida albicans* isolates from a patient infected with human immunodeficiency virus. *Antimicrob. Agents Chemother.* 41:14821487.

White, T. 1997b. The presence of an R467K amino acid substitution and loss of allelic variation correlate with an azole-resistant lanosterol 14a demethylase in *Candida albicans*. *Antimicrob. Agents Chemother.* 41:1488–1494.

All publications and patents are incorporated by reference herein, as though individually incorporated by reference, as long as they are not inconsistent with the present disclosure. The invention is not limited to the exact details shown and described, for it should be understood that many variations and modifications may be made while remaining within the spirit and scope of the invention defined by the claims.

What is claimed is:

1. An isolated nucleic acid segment comprising a nucleic acid sequence encoding a *Candida albicans* sterol methyltransferase having SEQ ID NO:2, a biologically active variant or subunit thereof, wherein the nucleic acid sequence specifically hybridizes under stringent conditions to SEQ ID NO:1 or the complement thereof.

2. The isolated nucleic acid segment of claim 1 which comprises a DNA sequence comprising SEQ ID NO:1.

3. The isolated nucleic acid segment of claim 1 which encodes a polypeptide having SEQ ID NO:2.

4. A recombinant isolate of *Candida albicans*, the genome of which does not encode a functional sterol methyltransferase.

5. The isolate of claim 4 in which at least one sterol methyltransferase gene has been disrupted by an insertion of DNA.

6. A recombinant isolate of *Candida albicans*, in which one genomic copy of the sterol methyltransferase gene does not encode a functional sterol methyltransferase.

7. The isolate of claim 4 or 6 which is susceptible to terbinafine, tridemorph, fenpropriomorph, fluphenazine, cycloheximide, cerulenin or brefeldin A relative to the susceptibility of the corresponding isolate of *Candida albicans* that has two copies of a sterol methyl transferase gene, each of which encodes a functional sterol methyltransferase.

8. The isolate of claim 4 or 6 which has increased permeability to antifungal agents or metabolic inhibitors.

9. The isolate of claim 4 or 6 in which the amount or activity of sterol methyltransferase is reduced or decreased relative to the amount or activity of sterol methyltransferase in an isolate that has two copies of a sterol methyl transferase gene, each of which encodes a functional sterol methyltransferase.

10. A method to identify inhibitors of fungal sterol methyltransferase, comprising:
(a) contacting an isolate of *Candida albicans*, the genome of which has two copies of a sterol methyltransferase gene, with an amount of an agent, wherein both copies of the gene are expressed at wild type levels; and (b) determining or detecting whether the agent inhibits the growth of the isolate relative to the inhibition of the growth of a corresponding recombinant *Candida albicans* isolate which has more than two copies of a functional sterol methyltransferase gene and has increased activity or amounts of functional sterol methyltransferase relative to the isolate of step (a).

11. The method of claim 10 wherein the recombinant isolate is stably transformed with an expression cassette which encodes a sterol methyltransferase.

12. The method of claim 11 wherein the expression cassette comprises SEQ ID NO:1.

13. A method to identify an anti-fungal agent which has reduced permeability to a wild type isolate of *Candida albicans*, comprising:

(a) contacting the isolate of claim 4 or 6 with an amount of the agent; and (b) determining or detecting whether the agent inhibits the growth of the isolate relative to the corresponding wild type *Candida albicans* isolate.

14. The method of claim 13 wherein the agent is a metabolic inhibitor.

15. The method of claim 13 wherein the agent is a polyene, allylamine or morpholine.

16. An isolated DNA segment comprising a DNA sequence having SEQ ID NO:1 or its complement, a portion thereof or a variant thereof, which portion or variant specifically hybridizes under stringent conditions to SEQ ID NO:1 or its complement.

17. The isolated DNA segment of claim 16 wherein the variant DNA segment encodes a polypeptide having SEQ ID NO:2.

* * * * *

UNITED STATES PATENT AND TRADEMARK OFFICE
CERTIFICATE OF CORRECTION

PATENT NO.    : 6,225,075 B1
DATED         : May 1, 2001
INVENTOR(S)   : Bard

It is certified that error appears in the above-identified patent and that said Letters Patent is hereby corrected as shown below:

Column 14,
Line 31, delete "DH5Δ" and insert -- DH5α --, therefor.

Column 15,
Line 10, delete "arc" and insert -- are --, therefor.

Signed and Sealed this

Eleventh Day of December, 2001

*Attest:*

NICHOLAS P. GODICI
*Attesting Officer*   Acting Director of the United States Patent and Trademark Office

SEQUENCE LISTING

<160> NUMBER OF SEQ ID NOS: 9

<210> SEQ ID NO 1
<211> LENGTH: 1400
<212> TYPE: DNA
<213> ORGANISM: Candida albicans

<400> SEQUENCE: 1

```
atacaaaatt tctttctttc cttttttact tttacaatta tttaaatcaa gttaaagaac      60 ctttcattt  cttattttaa tttaatttag aaattttcaa cctaattaat tcataatcta     120
agattcaact cattaacaat gtctccagtt caattagcag aaaaaaatta cgaaagagat     180
gaacaattca ctaaagcttt acatggtgaa tcttataaaa aaactgggtt atcagcttta     240
atagctaaat ctaaagatgc tgcttctgtt gctgctgagg gttatttcaa acattgggat     300
ggtggtattt ctaaagatga tgaagagaaa agattgaatg attattccca attgactcat     360
cattattata atttagtcac tgacttttat gaatatggtt ggggttcttc attccatttt     420
tcaagatatt ataaaggtga agcttttaga caagctactg ctagacatga acatttcttg     480
gcccataaaa tgaatcttaa tgaaaacatg aaagttttag atgttggttg tggtgtaggt     540
ggtcctggta gagaaatcac aagatttact gattgtgaaa ttgttggatt aaataataat     600
gattatcaaa ttgaaagagc taatcattat gctaaaaaat accatttaga tcataaatta     660
tcttatgtta aaggtgattt tatgcaaatg gattttgaac cagaatcatt cgatgctgtt     720
tatgccattg aagctaccgt tcatgctcca gttttagaag gagtttattc agaaatttat     780
aaagttttga aaccaggtgg tattttcggt gtttatgaat gggtcatgac tgataaatac     840
gatgaaacta atgaagaaca tcgtaaaatt gcttatggta ttgaagtcgg tgatggtatt     900
ccaaaaatgt attctcgtaa agttgctgaa caagctttga aaaatgttgg atttgaaatt     960
```

-continued

```
gaatatcaaa aagatttggc tgatgttgat gatgaaattc cttggtatta tccattaagt   1020
ggtgatttga aattttgtca aacttttggt gattatttga ctgttttcag aacttcaaga   1080
attggtagat tcattactac tgaatcagtt ggtttaatgg aaaaaattgg tttagctcca   1140
aaaggttcta aacaagttac tcatgcttta gaagatgctg ctgttaattt agttgaaggt   1200
ggtagacaaa aattgtttac tccaatgatg ttgtacgttg ttagaaaacc attagaaaag   1260
aaagattaat ggggcttgac aaacaacaag taaggtgagt ttatgttggg ggtgttcaat   1320
tcgtgtatct attcatagag gtattgattt gcaatttgtt ttttgtttat tctatttatt   1380
attttaaata ctgtttatat                                                1400
```

<210> SEQ ID NO 2
<211> LENGTH: 376
<212> TYPE: PRT
<213> ORGANISM: Candida albicans

<400> SEQUENCE: 2

```
Met Ser Pro Val Gln Leu Ala Glu Lys Asn Tyr Glu Arg Asp Glu Gln
 1               5                  10                  15

Phe Thr Lys Ala Leu His Gly Glu Ser Tyr Lys Lys Thr Gly Leu Ser
                20                  25                  30

Ala Leu Ile Ala Lys Ser Lys Asp Ala Ala Ser Val Ala Ala Glu Gly
            35                  40                  45

Tyr Phe Lys His Trp Asp Gly Gly Ile Ser Lys Asp Asp Glu Glu Lys
        50                  55                  60

Arg Leu Asn Asp Tyr Ser Gln Leu Thr His His Tyr Tyr Asn Leu Val
 65                  70                  75                  80

Thr Asp Phe Tyr Glu Tyr Gly Trp Gly Ser Ser Phe His Phe Ser Arg
                85                  90                  95

Tyr Tyr Lys Gly Glu Ala Phe Arg Gln Ala Thr Ala Arg His Glu His
            100                 105                 110

Phe Leu Ala His Lys Met Asn Leu Asn Glu Asn Met Lys Val Leu Asp
        115                 120                 125

Val Gly Cys Gly Val Gly Gly Pro Gly Arg Glu Ile Thr Arg Phe Thr
130                 135                 140

Asp Cys Glu Ile Val Gly Leu Asn Asn Asn Asp Tyr Gln Ile Glu Arg
145                 150                 155                 160

Ala Asn His Tyr Ala Lys Lys Tyr His Leu Asp His Lys Leu Ser Tyr
                165                 170                 175

Val Lys Gly Asp Phe Met Gln Met Asp Phe Glu Pro Glu Ser Phe Asp
            180                 185                 190

Ala Val Tyr Ala Ile Glu Ala Thr Val His Ala Pro Val Leu Glu Gly
        195                 200                 205

Val Tyr Ser Glu Ile Tyr Lys Val Leu Lys Pro Gly Gly Ile Phe Gly
    210                 215                 220

Val Tyr Glu Trp Val Met Thr Asp Lys Tyr Asp Glu Thr Asn Glu Glu
225                 230                 235                 240

His Arg Lys Ile Ala Tyr Gly Ile Glu Val Gly Asp Gly Ile Pro Lys
                245                 250                 255

Met Tyr Ser Arg Lys Val Ala Glu Gln Ala Leu Lys Asn Val Gly Phe
            260                 265                 270

Glu Ile Glu Tyr Gln Lys Asp Leu Ala Asp Val Asp Asp Glu Ile Pro
        275                 280                 285

Trp Tyr Tyr Pro Leu Ser Gly Asp Leu Lys Phe Cys Gln Thr Phe Gly
```

```
            290                 295                 300
Asp Tyr Leu Thr Val Phe Arg Thr Ser Arg Ile Gly Arg Phe Ile Thr
305                 310                 315                 320

Thr Glu Ser Val Gly Leu Met Glu Lys Ile Gly Leu Ala Pro Lys Gly
                325                 330                 335

Ser Lys Gln Val Thr His Ala Leu Glu Asp Ala Ala Val Asn Leu Val
            340                 345                 350

Glu Gly Gly Arg Gln Lys Leu Phe Thr Pro Met Met Leu Tyr Val Val
        355                 360                 365

Arg Lys Pro Leu Glu Lys Lys Asp
    370                 375

<210> SEQ ID NO 3
<211> LENGTH: 383
<212> TYPE: PRT
<213> ORGANISM: Saccharomyces cerevisiae

<400> SEQUENCE: 3

Met Ser Glu Thr Glu Leu Arg Lys Arg Gln Ala Gln Phe Thr Arg Glu
1               5                   10                  15

Leu His Gly Asp Asp Ile Gly Lys Lys Thr Gly Leu Ser Ala Leu Met
            20                  25                  30

Ser Lys Asn Asn Ser Ala Gln Lys Glu Ala Val Gln Lys Tyr Leu Arg
        35                  40                  45

Asn Trp Asp Gly Arg Thr Asp Lys Asp Ala Glu Arg Arg Leu Glu
    50                  55                  60

Asp Tyr Asn Glu Ala Thr His Ser Tyr Tyr Asn Val Val Thr Asp Phe
65                  70                  75                  80

Tyr Glu Tyr Gly Trp Gly Ser Ser Phe His Phe Ser Arg Phe Tyr Lys
                85                  90                  95

Gly Glu Ser Phe Ala Ala Ser Ile Ala Arg His Glu His Tyr Leu Ala
            100                 105                 110

Tyr Lys Ala Gly Ile Gln Arg Gly Asp Leu Val Leu Asp Val Gly Cys
        115                 120                 125

Gly Val Gly Gly Pro Ala Arg Glu Ile Ala Arg Phe Thr Gly Cys Asn
130                 135                 140

Val Ile Gly Leu Asn Asn Asn Asp Tyr Gln Ile Ala Lys Ala Lys Tyr
145                 150                 155                 160

Tyr Ala Lys Lys Tyr Asn Leu Ser Asp Gln Met Asp Phe Val Lys Gly
                165                 170                 175

Asp Phe Met Lys Met Asp Phe Glu Glu Asn Thr Phe Asp Lys Val Tyr
            180                 185                 190

Ala Ile Glu Ala Thr Cys His Ala Pro Lys Leu Glu Gly Val Tyr Ser
        195                 200                 205

Glu Ile Tyr Lys Val Leu Lys Pro Gly Gly Thr Phe Ala Val Tyr Glu
    210                 215                 220

Trp Val Met Thr Asp Lys Tyr Asp Glu Asn Asn Pro Glu His Arg Lys
225                 230                 235                 240

Ile Ala Tyr Glu Ile Glu Leu Gly Asp Gly Ile Pro Lys Met Phe His
                245                 250                 255

Val Asp Val Ala Arg Lys Ala Leu Lys Asn Cys Gly Phe Glu Val Leu
            260                 265                 270

Val Ser Glu Asp Leu Ala Asp Asn Asp Asp Glu Ile Pro Trp Tyr Tyr
        275                 280                 285
```

```
Pro Leu Thr Gly Glu Trp Lys Tyr Val Gln Asn Leu Ala Asn Leu Ala
    290                 295                 300

Thr Phe Phe Arg Thr Ser Tyr Leu Gly Arg Gln Phe Thr Thr Ala Met
305                 310                 315                 320

Val Thr Val Met Glu Lys Leu Gly Leu Ala Pro Glu Gly Ser Lys Glu
                325                 330                 335

Val Thr Ala Ala Leu Glu Asn Ala Ala Val Gly Leu Val Ala Gly Gly
                340                 345                 350

Lys Ser Lys Leu Phe Thr Pro Met Met Leu Phe Val Ala Arg Lys Pro
                355                 360                 365

Glu Asn Ala Glu Thr Pro Ser Gln Thr Ser Gln Glu Ala Thr Gln
                370                 375                 380

<210> SEQ ID NO 4
<211> LENGTH: 361
<212> TYPE: PRT
<213> ORGANISM: Arabidopsis thaliana

<400> SEQUENCE: 4

Met Asp Ser Leu Thr Leu Phe Phe Thr Gly Ala Leu Val Ala Val Gly
1               5                   10                  15

Ile Tyr Trp Phe Leu Cys Val Leu Gly Pro Ala Glu Arg Lys Gly Lys
                20                  25                  30

Arg Ala Val Asp Leu Ser Gly Gly Ser Ile Ser Ala Glu Lys Val Gln
            35                  40                  45

Asp Asn Tyr Lys Gln Tyr Trp Ser Phe Phe Arg Arg Pro Lys Glu Ile
        50                  55                  60

Glu Thr Ala Glu Lys Val Pro Asp Phe Val Asp Thr Phe Tyr Asn Leu
65                  70                  75                  80

Val Thr Asp Ile Tyr Glu Trp Gly Trp Gly Gln Ser Phe His Phe Ser
                85                  90                  95

Pro Ser Ile Pro Gly Lys Ser His Lys Asp Ala Thr Arg Leu His Glu
                100                 105                 110

Glu Met Ala Val Asp Leu Ile Gln Val Lys Pro Gly Gln Lys Ile Leu
            115                 120                 125

Asp Val Gly Cys Gly Val Gly Gly Pro Met Arg Ala Ile Ala Ser His
130                 135                 140

Ser Arg Ala Asn Val Val Gly Ile Thr Ile Asn Glu Tyr Gln Val Asn
145                 150                 155                 160

Arg Ala Arg Leu His Asn Lys Lys Ala Gly Leu Asp Ala Leu Cys Glu
                165                 170                 175

Val Val Cys Gly Asn Phe Leu Gln Met Pro Phe Asp Asp Asn Ser Phe
            180                 185                 190

Asp Gly Ala Tyr Ser Ile Glu Ala Thr Cys His Ala Pro Lys Leu Glu
        195                 200                 205

Glu Val Tyr Ala Glu Ile Tyr Arg Val Leu Lys Pro Gly Ser Met Tyr
    210                 215                 220

Val Ser Tyr Glu Trp Val Thr Thr Glu Lys Phe Lys Ala Glu Asp Asp
225                 230                 235                 240

Glu His Val Glu Val Ile Gln Gly Ile Glu Arg Gly Asp Ala Leu Pro
                245                 250                 255

Gly Leu Arg Ala Tyr Val Asp Ile Ala Glu Thr Ala Lys Lys Val Gly
            260                 265                 270

Phe Glu Ile Val Lys Glu Lys Asp Leu Ala Ser Pro Pro Ala Glu Pro
        275                 280                 285
```

```
Trp Trp Thr Arg Leu Lys Met Gly Arg Leu Ala Tyr Trp Arg Asn His
    290                 295                 300

Ile Val Val Gln Ile Leu Ser Ala Val Gly Val Ala Pro Lys Gly Thr
305                 310                 315                 320

Val Asp Val His Glu Met Leu Phe Lys Thr Ala Asp Cys Leu Thr Arg
                325                 330                 335

Gly Gly Glu Thr Gly Ile Phe Ser Pro Met His Met Ile Leu Cys Arg
                340                 345                 350

Lys Pro Glu Ser Pro Glu Glu Ser Ser
                355                 360

<210> SEQ ID NO 5
<211> LENGTH: 363
<212> TYPE: PRT
<213> ORGANISM: Triticum atrivum

<400> SEQUENCE: 5

Met Phe Val Phe Cys Leu Cys Thr Arg Cys Arg Ile Cys Arg Val Ser
  1               5                  10                  15

Ser Phe Pro Val Leu Leu Leu Phe Met Phe Ile His Leu Ser Tyr Phe
                 20                  25                  30

Phe Leu Val Leu Leu Leu Ile Leu Gly Gln Phe Phe Thr Arg Tyr
             35                  40                  45

Glu Lys Tyr His Gly Tyr Tyr Gly Gly Lys Glu Glu Ser Arg Lys Ser
     50                  55                  60

Asn Tyr Thr Asp Met Val Asn Lys Tyr Tyr Asp Leu Ala Thr Ser Phe
 65                  70                  75                  80

Tyr Glu Tyr Gly Trp Gly Glu Ser Phe His Phe Ala His Arg Trp Asn
                 85                  90                  95

Gly Glu Ser Leu Arg Glu Ser Ile Lys Arg His Glu His Phe Leu Ala
                100                 105                 110

Leu Gln Leu Glu Leu Lys Pro Gly Met Lys Val Leu Asp Val Gly Cys
            115                 120                 125

Gly Ile Gly Gly Pro Leu Arg Glu Ile Ala Arg Phe Ser Ser Thr Ser
        130                 135                 140

Val Thr Gly Leu Asn Asn Asn Asp Tyr Gln Ile Thr Arg Gly Lys Ala
145                 150                 155                 160

Leu Asn Arg Ser Val Gly Leu Gly Ala Thr Cys Asp Phe Val Lys Ala
                165                 170                 175

Asp Phe Met Lys Met Pro Phe Ser Asp Asn Thr Phe Asp Ala Val Tyr
                180                 185                 190

Ala Ile Glu Ala Thr Cys His Ala Pro Asp Pro Val Gly Cys Tyr Lys
            195                 200                 205

Glu Ile Tyr Arg Val Leu Lys Pro Gly Gln Cys Phe Ala Val Tyr Glu
        210                 215                 220

Trp Cys Ile Thr Asp His Tyr Asp Pro Asn Asn Ala Thr His Lys Arg
225                 230                 235                 240

Ile Lys Asp Glu Ile Glu Leu Gly Asn Gly Leu Pro Asp Ile Arg Ser
                245                 250                 255

Thr Arg Gln Cys Leu Gln Ala Val Lys Asp Ala Gly Phe Glu Val Ile
                260                 265                 270

Trp Asp Lys Asp Leu Ala Glu Asp Ser Pro Leu Pro Trp Tyr Leu Pro
            275                 280                 285

Leu Asp Pro Ser Arg Phe Ser Leu Ser Ser Phe Arg Leu Thr Thr Val
```

```
                   290                 295                 300
Gly Arg Ile Ile Thr Arg Asn Met Val Lys Val Leu Glu Tyr Val Gly
305                 310                 315                 320

Leu Ala Pro Glu Gly Ser Gln Arg Val Ser Ser Phe Leu Glu Lys Ala
                325                 330                 335

Ala Glu Gly Leu Val Glu Gly Gly Lys Lys Glu Ile Phe Thr Pro Met
                340                 345                 350

Tyr Phe Phe Val Val Arg Lys Pro Leu Ser Glu
            355                 360

<210> SEQ ID NO 6
<211> LENGTH: 17
<212> TYPE: DNA
<213> ORGANISM: Candida albicans

<400> SEQUENCE: 6
cacatgggtg aaattag                                                 17

<210> SEQ ID NO 7
<211> LENGTH: 18
<212> TYPE: DNA
<213> ORGANISM: Candida albicans

<400> SEQUENCE: 7
ctccagttca attagcag                                                18

<210> SEQ ID NO 8
<211> LENGTH: 18
<212> TYPE: DNA
<213> ORGANISM: Candida albicans

<400> SEQUENCE: 8
tgtgcgtgta caaagcac                                                18

<210> SEQ ID NO 9
<211> LENGTH: 18
<212> TYPE: DNA
<213> ORGANISM: Candida albicans

<400> SEQUENCE: 9
gataataccg agatcgac                                                18
```